(12) United States Patent
Salamon et al.

(10) Patent No.: US 6,421,128 B1
(45) Date of Patent: *Jul. 16, 2002

(54) COUPLED PLASMON-WAVEGUIDE RESONANCE SPECTROSCOPIC DEVICE AND METHOD FOR MEASURING FILM PROPERTIES IN THE ULTRAVIOLET AND INFRARED SPECIAL RANGES

(75) Inventors: Zdzislaw Salamon; Gordon Tollin, both of Tucson, AZ (US)

(73) Assignee: The Arizona Board of Regents on behalf of the University of Arizona, Tucson, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/572,156

(22) Filed: May 17, 2000

(51) Int. Cl.$^7$ ................................................ G01N 21/55
(52) U.S. Cl. ...................................................... 356/445
(58) Field of Search ......................................... 356/445

(56) References Cited

U.S. PATENT DOCUMENTS

| | | | |
|---|---|---|---|
| 5,017,007 A | 5/1991 | Milne et al. | 356/301 |
| 5,116,121 A | 5/1992 | Knoll et al. | 356/301 |
| 5,327,225 A | * 7/1994 | Bender et al. | 356/445 |
| 5,344,784 A | 9/1994 | Attridge | 436/518 |
| 5,478,755 A | * 12/1995 | Attridge et al. | 356/317 |
| 5,521,702 A | 5/1996 | Salamon et al. | 356/244 |
| 5,563,707 A | 10/1996 | Prass et al. | 356/361 |
| 5,606,633 A | * 2/1997 | Groger et al. | 385/12 |
| 5,792,667 A | 8/1998 | Florin et al. | 436/147 |
| 5,846,843 A | 12/1998 | Simon | 436/527 |
| 5,991,488 A | * 11/1999 | Salamon | 385/129 |

OTHER PUBLICATIONS

Salamon et al., "Surface Plasmon Resonance, Theory," Encyclopedia of Spectroscopy & Spectrometry, Academic Press, vol. 3, 2311–2319.

Salamon et al., "Surface Plasmon Resonance: Applications," Encyclopedia of Spectroscopy & Spectrometry, Academic Press, vol. 3, 2294–2302.

Salamon et al., "Plasmon Resonance Spectroscopy: Probing Molecular Interactions within Membranes," Trends in Biochemical Sciences, 24, 213–219 (1999).

* cited by examiner

Primary Examiner—Richard A. Rosenberger
(74) Attorney, Agent, or Firm—Antonio R. Durando

(57) ABSTRACT

A metallic (or semiconductor) layer (or layers) is used with either a prism or a grating so as to provide a surface plasmon wave under total reflection conditions of an incident light of predetermined wavelength outside the visible spectrum. The metal layer is selected with a refractive index as small as possible and an extinction coefficient as large as possible within the wavelength of interest and is covered with a solid dielectric layer characterized by predetermined optical parameters. This layer may contain one or several layers of different materials and plays the role of a light waveguide that generates waveguide modes coupled to surface plasmons, resulting in a new set of resonances excited by both p- and s-polarized excitation light and characterized by much narrower spectra than produced by conventional SPR. In a particular embodiment of the invention, the dielectric layer may be designed to serve both as a waveguide and at the same time as an electrode. This allows the combination of an optical device with an electrical device, capable of monitoring simultaneously electrical characteristics and optical parameters of thin films and interfaces.

30 Claims, 16 Drawing Sheets

LR-CPWR

IR-CPWR

CPWR

LR-CPWR

COUPLED PLASMON-WAVEGUIDE RESONANCE SPECTROSCOPIC DEVICE AND METHOD FOR MEASURING FILM PROPERTIES IN THE ULTRAVIOLET AND INFRARED SPECIAL RANGES

RELATED APPLICATIONS

This application is a continuation-in-part application of U.S. application Ser. No. 09/448,394 filed on Nov. 23, 1999, pending, which is a CIP of Ser. No. 08/965,733, filed on Nov. 7, 1997, U.S. Pat. No. 5,991,488, which was based on Provisional Application No. 60/030,768, filed on Nov. 8, 1996.

U.S. GOVERNMENT RIGHTS

This invention was made with Federal Government support under contract number MCB-9904753 awarded by the National Science Foundation. The Government has certain rights in the invention.

BACKGROUND OF THE INVENTION

1. Field of the Invention

This invention pertains in general to the field of surface plasmon resonance (SPR) spectroscopy. In particular, the invention relates to a novel SPR approach involving the coupling of plasmon resonances in a thin metal film and the waveguide modes in a dielectric overcoating in the ultraviolet and infrared electromagnetic spectral ranges.

2. Description of the Related Art

Surface plasmon resonance is a phenomenon used in many analytical applications in metallurgy, microscopy, and chemical and biochemical sensing. With optical techniques such as ellipsometry, multiple internal reflection spectroscopy, and differential reflectivity, SPR is one of the most sensitive techniques to surface and interface effects. This inherent property makes SPR well suited for nondestructive studies of surfaces, interfaces, and very thin layers. SPR is also used in other than surface investigations and it has recently been demonstrated as a new optical technique for use in immunoassays.

The SPR phenomenon has been known for decades and the theory is fairly well developed. Simply stated, a surface plasmon is an oscillation of free electrons that propagates along the surface of a conductor. The phenomenon of surface plasmon resonance occurs under total internal reflection conditions at the boundary between substances of different refractive indices, such as glass and water solutions. When an incident light beam is reflected internally within the first medium, its electromagnetic field produces an evanescent wave that crosses a short distance (in the order of nanometers) beyond the interface with the second medium. If a thin metal film is inserted at the interface between the two media, surface plasmon resonance occurs when the free electron clouds in the metal layer (the plasmons) absorb energy from the evanescent wave and cause a measurable drop in the intensity of the reflected light at a particular angle of incidence that depends on the refractive index of the second medium.

Typically, the conductor used for SPR spectrometry is a thin film of metal such as silver or gold; however, surface plasmons have also been excited on semiconductors. The conventional method of exciting surface plasmons is to couple the transverse-magnetic (TM) polarized energy contained in an evanescent field to the plasmon mode on a metal film. The amount of coupling, and thus the intensity of the plasmon, is determined by the incident angle of the light beam and is directly affected by the refractive indices of the materials on both sides of the metal film. By including the sample material to be measured as a layer on one side of the metallic film, changes in the refractive index of the sample material can be monitored by measuring changes in the surface plasmon coupling efficiency in the evanescent field. When changes occur in the refractive index of the sample material, the propagation of the evanescent wave and the angle of incidence producing resonance are affected. Therefore, by monitoring the angle of incidence at a given wavelength and identifying changes in the angle that causes resonance, corresponding changes in the refractive index and related properties of the material can be readily detected.

As those skilled in the field readily understand, total reflection can only occur above a particular critical incidence angle if the refractive index of the incident medium (a prism or grating) is greater than that of the emerging medium. In practice, total reflection is observed only for incidence angles within a range narrower than from the critical angle to 90 degrees because of the physical limitations inherent with the testing apparatus. Similarly, for systems operating with variable wavelengths and a given incidence angle, total reflection is also observed only for a corresponding range of wavelengths. This range of incidence angles (or wavelengths) is referred to as the "observable range" for the purpose of this disclosure. Moreover, a metal film with a very small refractive index (as small as possible) and a very large extinction coefficient (as large as possible) is required to support plasmon resonance. Accordingly, gold and silver are appropriate materials for the thin metal films used in visible-light SPR; in addition, they are very desirable because of their mechanical and chemical resistance.

Thus, once materials are selected for the prism, metal film and emerging medium that satisfy the described conditions for total reflection and plasmon resonance, the reflection of a monochromatic incident beam becomes a function of its angle of incidence and of the metal's refractive index, extinction coefficient, and thickness. The thickness of the film is therefore selected such that it produces observable plasmon resonance when the monochromatic light is incident at an angle within the observable range.

The classical embodiments of SPR devices are the Kretschmann and Otto prism or grating arrangements, which consist of a prism with a high refractive index n (in the 1.4–1.7 range) coated on one face with a thin film of metal. The Otto device also includes a very thin air gap between the face of the prism and the metal film. In fact, the gap between the prism (or grating) and the metal layer, which is in the order of nanometers, could be of a material other than air, even metal, so long as compatible with the production of observable plasmon resonance in the metal film when the monochromatic light is incident at an angle within the observable range.

Similar prior-art SPR devices are based on the phenomenon of long-range surface plasmon resonance, which is also generated with p-polarized light using a dielectric medium sandwiched between the incident medium and a thinner metal layer (than in conventional SPR applications). The metal film must be sufficiently thin and the dielectric and emergent media must be beyond the critical angle (i.e., having refractive indices smaller than the refractive index of the entrant medium) so that they support evanescent waves to permit the simultaneous coupling of surface plasmons at the top and bottom interfaces of the thin metal layer (i.e., to permit excitation of surface waves on both sides of the thin metal film). This condition is necessary in order for the phenomenon of long-range surface plasmon resonance to occur. For a given set of parameters, the distinguishing structural characteristic between conventional surface plasmon resonance and long-range surface plasmon resonance is the thickness of the metal film and of the inner dielectric film (the latter not being necessary for conventional SPR). In the conventional technique, the metal film must be sufficiently thick and must be placed either directly on the entrant medium (i.e., prism or grating), or on a dielectric film which is too thin, to allow excitation of the surface bound waves on both metal surfaces to produce observable plasmon resonance when a monochromatic light is incident at an angle within the observable range. In long-range surface plasmon resonance (LRSPR), in contrast, the metal film must be placed between two dielectric media that are beyond the critical angle so that they support evanescent waves, and must be thin enough to permit excitation of surface waves on both sides of the metal film. The specific thickness depends on the optical parameters of the various components of the sensor in question, but film thicknesses in the order of 45–55 nm for gold and silver are recognized as critical for conventional SPR, while no more than about half as much (15–28 nm) can be used for LRSPR. It is noted that the thickness required to support either form of surface plasmon resonance for a specific system can be calculated by one skilled in the art on the basis of the system's optical parameters.

As well understood by those skilled in the art, the main criterion for a material to support SP waves is that it have a negative real dielectric component, which results from the refractive and extinction properties mentioned above for the metal layer. The surface of the metal film forms the transduction mechanism for the SPR device and is brought into contact with the sample material to be sensed at the interface between the metal film and the emerging medium contained in a cell assembly. Monochromatic light is emitted by a laser or equivalent light source into the prism or grating and reflected off the metal film to an optical photodetector to create the sensor output. The light launched into the prism and coupled into the SP mode on the film is p-polarized with respect to the metal surface where the reflection takes place. In all these prior-art devices and techniques, only p-polarized light is coupled into the plasmon mode because this particular polarization has the electric field vector oscillating normal to the plane that contains the metal film. This is sometimes referred to as transverse-magnetic (TM) polarization.

As mentioned, the surface plasmon is affected by changes in the dielectric value of the material in contact with the metal film. As this value changes, the conditions necessary to couple light into the plasmon mode also change. Thus, SPR is used as a highly sensitive technique for investigating changes that occur at the surface of the metal film. In particular, over the last several years there has been a keen interest in the application of surface plasmon resonance spectroscopy to study the optical properties of molecules immobilized at the interface between solid and liquid phases. The ability of the SPR phenomenon to provide information about the physical properties of dielectric thin films deposited on a metal layer, including lipid and protein molecules forming proteolipid membranes, is based upon two principal characteristics of the SPR effect. The first is the fact that the evanescent electromagnetic field generated by the free electron oscillations decays exponentially with penetration distance into the emergent dielectric medium; i.e., the depth of penetration into the material in contact with a metal layer extends only to a fraction of the light wavelength used to generate the plasmons. This makes the phenomenon sensitive to the optical properties of the metal/dielectric interface without any interference from the properties of the bulk volume of the dielectric material or any medium that is in contact with it. The second characteristic is the fact that the angular (or wavelength) position and shape of the resonance curve is very sensitive to the optical properties of both the metal film and the emergent dielectric medium adjacent to the metal surface. As a consequence of these characteristics, SPR is ideally suited for studying both structural and mass changes of thin dielectric films, including lipid membranes, lipid-membrane/protein interactions, and interactions between integral membrane proteins and peripheral, water-soluble proteins. See Salamon, Z., H. A. Macleod and G. Tollin, "Surface Plasmon Resonance Spectroscopy as a Tool for Investigating the Biochemical and Biophysical Properties of Membrane Protein Systems. I: Theoretical Principles," *Biochim. et Biophys. Acta,* 1331: 117–129 (1997); and Salamon, Z., H. A. Macleod and G. Tollin, "Surface Plasmon Resonance Spectroscopy as a Tool for Investigating the Biochemical and Biophysical Properties of Membrane Protein Systems. II: Applications to Biological Systems," *Biochim. et Biophys. Acta,* 1331: 131–152 (1997).

In U.S. Pat. No. 5,991,488, herein incorporated by reference, we disclosed new thin-film interface designs that couple surface plasmon and waveguide excitation modes. The new technique, defined as coupled plasmon-waveguide resonance (CPWR), is based on the totally new concept of coupling plasmon resonances in a thin metal film with the waveguide modes in a dielectric overcoating. Accordingly, a metallic layer, typically either gold or silver, is used with a prism so as to provide a surface plasmon wave by conventional SPR (or waves by long-range SPR) and is further covered with a solid dielectric layer characterized by predetermined optical parameters. The dielectric member inserted between the metal film and the emergent medium is selected such that coupled plasmon-waveguide resonance effects are produced within an observable range. The emergent dielectric medium is then placed in contact with this solid dielectric layer. We found that the additional layer of dielectric material functions as an optical amplifier that produces an increased sensitivity and enhanced spectroscopic capabilities in SPR. In particular, the added dielectric layer makes it possible to produce resonance with either s- or p-polarized light. In addition, the added dielectric protects the metal layer and can be used as a matrix for adsorbing and immobilizing the sensing materials in sensor applications. This disclosure provides a further improvement in coupled plasmon-waveguide resonance that constitutes material advances in the art of SPR.

BRIEF SUMMARY OF THE INVENTION

The main goal of this invention is the extension of coupled plasmon-waveguide resonance to a wider range of electromagnetic-spectrum applications.

In particular, a goal of the invention is the ability to perform SPR, long-range SPR, and CPWR in the ultraviolet and infrared spectral ranges in order to enable the testing of materials sensitive to specific UV and IF wavelengths.

Another object is a CPWR technique that permits the practice of surface plasmon resonance both with s- and p-polarized light.

Another goal is a CPWR technique that provides the ability to measure anisotropy of both the refractive index and the extinction coefficient of a medium of interest at any wavelength.

Another important objective is a technique that is suitable for testing a wide range of materials, especially lipid membranes that have either integral membrane proteins incorporated into them or peripheral membrane proteins bound to their surface.

Another goal of the invention is a tool that is particularly suitable for obtaining information about molecular assemblies that can be immobilized at a dielectric/water interface.

Another objective is a CPWR device that can serve both as a waveguide and at the same time as an electrode, capable of monitoring simultaneously electrical characteristics and optical parameters of thin films and interfaces.

Yet another objective is an approach that in the CPWR embodiments provides protection of the plasmon-generating metallic film against mechanical or chemical deterioration during use.

Another goal is a technique that makes it possible to achieve the objectives of the invention with an efficient, practical and economically feasible implementation.

Finally, another objective is a procedure and corresponding apparatus that are suitable for direct incorporation with existing SPR spectroscopic instruments.

Therefore, according to these and other objectives, the present invention consists of a metallic (or semiconductor) layer (or layers), used with either a prism or a grating so as to provide a surface plasmon wave under total reflection conditions of an incident light of predetermined wavelength outside the visible spectrum. The metal layer is selected with a refractive index as small as possible and an extinction coefficient as large as possible within the wavelength of interest and is covered on the emergent side with a solid dielectric layer characterized by predetermined optical parameters. Specifically, the dielectric member inserted between the metal layer and the emergent medium is selected such that coupled plasmon-waveguide resonance effects are produced within an observable range. This layer may contain one or several layers of different materials and plays the role of coupling waveguide modes to surface plasmon generation, resulting in a new set of resonances excited by both p- and s-polarized excitation light and characterized by much narrower spectra than produced by conventional SPR or LRSPR. In a particular embodiment of the invention, the dielectric layer may be designed to serve both as a waveguide and at the same time as an electrode. This allows the combination of an optical device with an electrical device, capable of monitoring simultaneously electrical characteristics and optical parameters of thin films and interfaces.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DESCRIPTION OF THE PREFERRED EMBODIMENTS OF THE INVENTION

Optical testing of thin films and interfaces is limited by the range of wavelength operation of the available testing devices. All prior-art SPR sensors, including long-range SPR sensors, and coupled plasmon-waveguide resonators (CPWRs), have been limited to visible light testing because of the characteristics of the materials making up the sensors. In fact, it would be very useful to be able to extend the range of wavelength used in performing SPR because many interesting, previously undetected, phenomena occur in analytes as a result of excitation in the UV or IF spectral range. This invention is based on the realization that SPR can be extended to those wavelengths simply by selecting the wavelength range of interest for a particular application, and then finding a metal or semiconductor material having the combined properties of an index of refraction as small as possible and a coefficient of extinction as large as possible. In addition, in order to practice the coupled plasmon-waveguide resonance techniques disclosed in U.S. Pat. No. 5,991,488, a dielectric layer is interposed between the metallic layer and the sample material.

The invention is described herein with reference to the CPWR disclosed in the referenced patent, but it is clear that it can be practiced equivalently with any prior-art SPR and long-range SPR device. It is also understood that the dielectric layer of the invention is in addition to and separate from the sample material or analyte with which the invention is used. The sample material at the interface with the emerging medium is often itself dielectric in nature, but its properties cannot be used to obtain the advantages of CPWR without the addition of an additional dielectric layer as disclosed in U.S. Pat. No. 5,991,488. Therefore, all references to dielectric material pertain only to the additional layer contemplated by CPWRs.

The term SPR is used in this disclosure to refer in general to all forms of surface plasmon resonance including, in particular, LRSPR. Similarly, the term CPWR is used to refer to all forms of coupled plasmon-waveguide resonance including, in particular, LRSPR.

Figure 1:
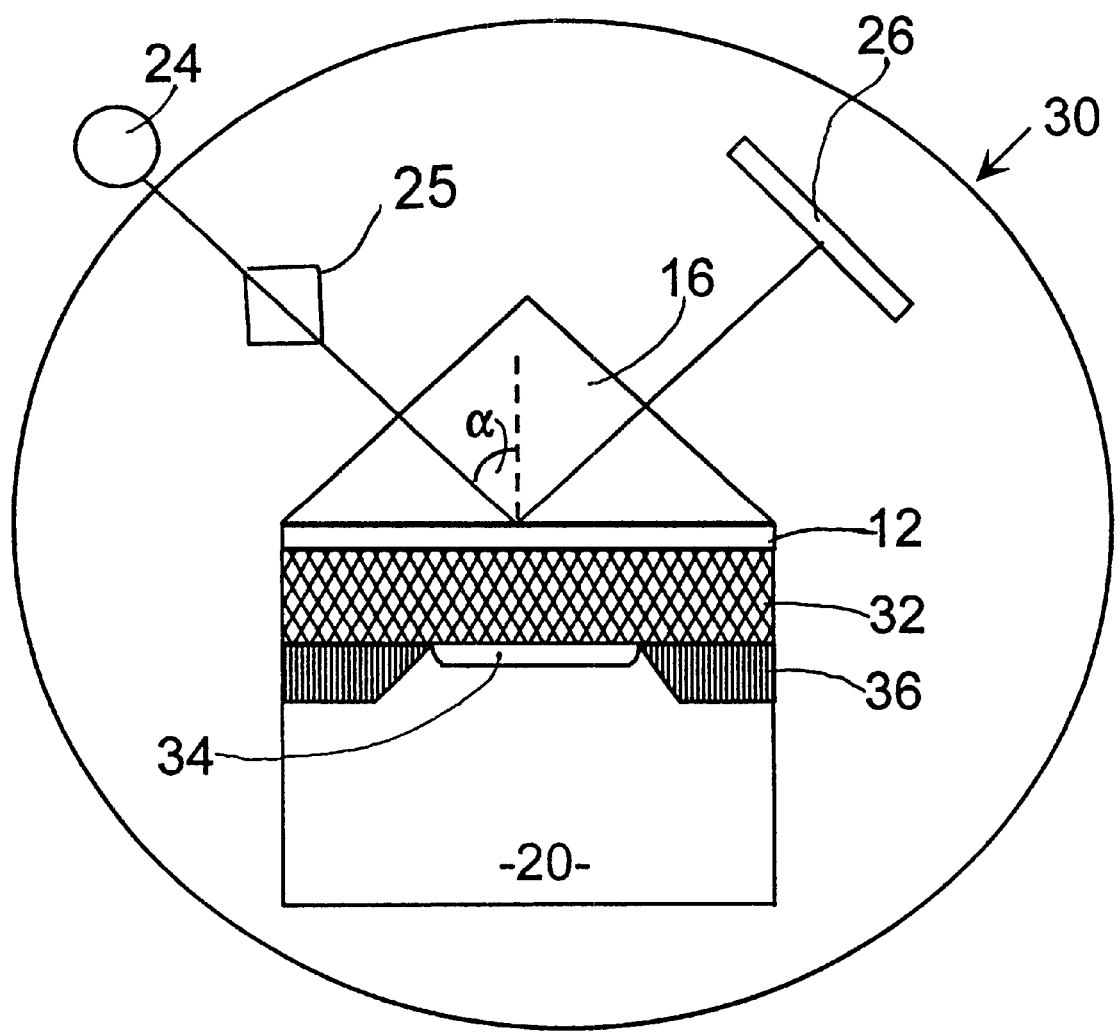
FIG. 1 is a schematic view of an embodiment of a coupled plasmon-waveguide resonance spectroscopic tool according to the invention in an attenuated total reflection measuring system, wherein a glass prism coated with a 50 nm-thick silver layer is protected by a 460 nm-thick $SiO_2$ film; a lipid bilayer is deposited on the dielectric film and held in place by a TEFLON® spacer.

Referring to the drawings, wherein like reference numerals and symbols are used for like parts, FIG. 1 illustrates in schematic form a CPWR device 30 according to a visible-light embodiment of the invention. The device 30 contains a metallic (or semiconductor) layer (or layers) 12, typically between 45 and 55 nm thick, formed from either gold or silver deposited on either a glass prism or grating 16 for generating a surface plasmon wave. Note that the same elements could be used in an Otto configuration with a very thin air (or other material) gap between the glass and metal layer. The silver film is covered with a layer 32 of solid dielectric material characterized by an appropriate set of values of film thickness, t, refractive index, n, and extinction coefficient, k.

Suitable dielectric materials must have a refraction index $n_d$ greater than the refractive index $n_e$ of the emerging medium; they must have an extinction coefficient $k_d$ as small as possible for a given wavelength (for example, $\leq 0.1$, preferably between 0 and 0.01, for $\lambda$=633 nm); and they must be selected with a thickness that will support a guided wave and result in resonance effects occurring at an angle of incidence within the observable range, as explained above. For example, a glass prism coated with a 50 nm-thick silver layer protected by a 460 nm-thick $SiO_2$ film ($n_d$=1.4571, $k_d$=0.0030) is suitable to practice the invention with an aqueous analyte ($n_e$=1.33). A lipid bilayer 34 (the material being tested) is deposited from the sample solution 20 on the dielectric film 32 and held in place by a TEFLON® spacer 36 according to the teachings of U.S. Pat. No. 5,521,702 (Salamon et al.).

In the $SiO_2$ embodiment of FIG. 1, with a wavelength of about 633 nm, the dielectric material must be at least 50 nm thick to act as a waveguide. In addition, the resulting s-resonance will fall within the observable range for any thickness larger than 250 nm; on the other hand, the p-resonance will be visible for any thickness greater than 400 nm. In order to fulfill the conditions of the invention for both types of polarization, the dielectric layer must be at least about 420 nm thick. Similarly, the same configuration embodied with a $TiO_2$ dielectric and a wavelength of about 633 nm would require a thickness larger than 65 nm for the s-resonance and larger than 140 nm for the p-resonance to be observable. The conditions of the invention would be met for both types of polarization with a $TiO_2$ layer at least 750 nm thick.

Figure 2:
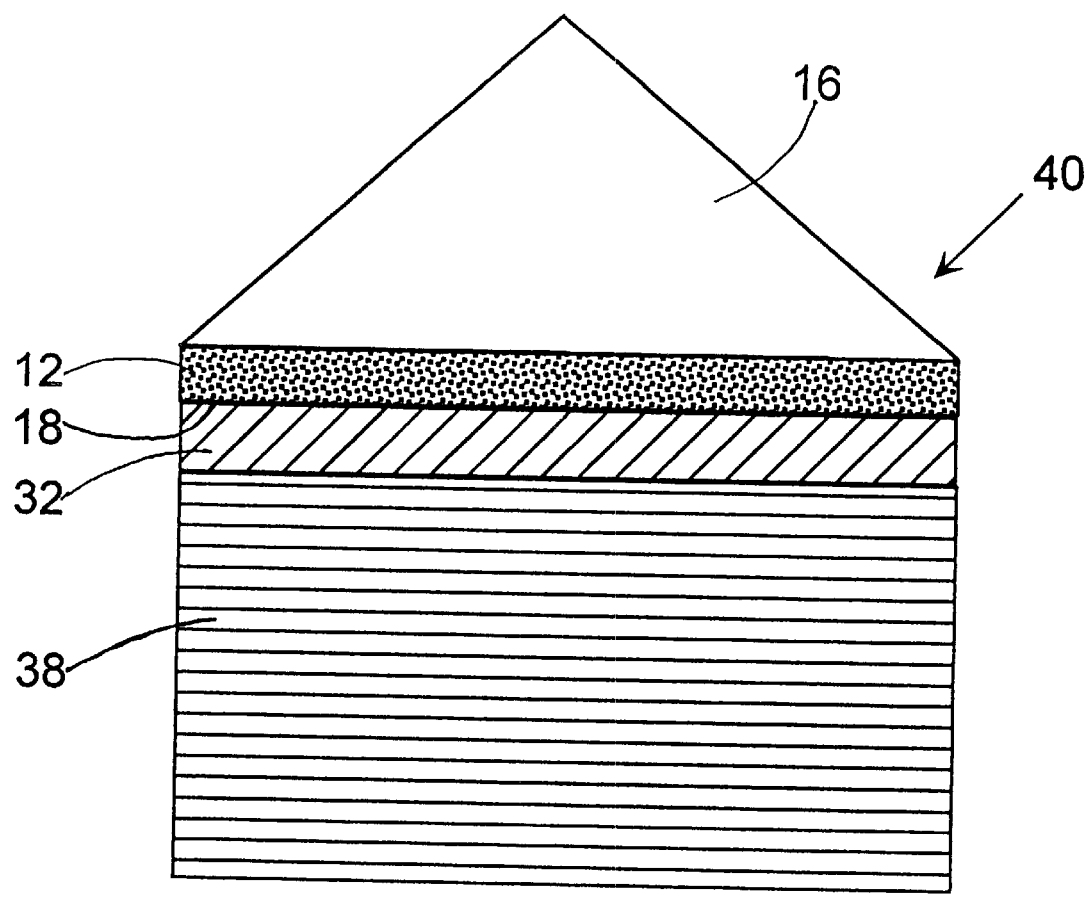
FIG. 2 is a schematic view of another embodiment of a coupled plasmon-waveguide resonance spectroscopic tool according to the invention, wherein a silver-coated glass prism contains two dielectric layers; one layer of 50 nm $TiO_2$ protects the silver film and is coated with a second 750 nm layer of a lower refractive-index dielectric material (n=1.35).

In another embodiment 40 of the invention, illustrated in FIG. 2, the silver-coated glass prism 16 includes two solid dielectric layers. One 50 nm layer 32 of $Tio_2$ ($n_d$=2.2789, $k_d$=0.000151) protects the silver film 12; a second 750 nm layer 38 of a lower density, lower refractive index (n=1.35) dielectric material ($Na_3AlF_6$) is applied over the first layer. In this example this material is selected with a lower density and a correspondingly higher porosity so as to provide a structural matrix for adsorbing and immobilizing the sensing materials 20 (hydrogels are well known materials used for this purpose).

According to one aspect of the CPWR invention first disclosed in U.S. Pat. No. 5,992,488, spectroscopic measurements with the devices 30 and 40 are based upon the resonant excitation of electromagnetic modes of the structure by both TM (p) and TE (s) polarized components of a continuous-wave laser light (e.g., He—Ne; $\lambda$=632.8 nm) passing through the glass prism 16 under total internal reflection conditions. We found that the addition of the dielectric layer 32, with the appropriate set of optical parameters defined above, to a conventional SPR arrangement not only provides both mechanical and chemical protection for the metal layer 12, but also produces optical amplification that results in increased sensitivity and enhanced spectroscopic capabilities.

Using the structures of FIGS. 1 and 2, it was possible to determine that the relative bandwidths of the resonances obtained with either p- or s-polarized incident light, and therefore the sensitivity of the measurement, can be varied by altering the properties of the overcoat film 32 (or films 32,38). Thus, this discovery makes it possible to both expand SPR spectroscopy to the use of s-polarized light and improve the quality of the measurements by altering the spectral response of the system. In addition, in sensor applications the added dielectric overcoat could also be used as a matrix that adsorbs and immobilizes the sensing material 20. For example, the DEXTRAN® layer that is currently used in commercial SPR biosensors for fast and efficient immobilization of ligands could be manipulated into the dielectric matrix 38 to generate resonances with widely varying sensitivities. See Salamon et al., II: Applications to Biological Systems, supra.

As detailed in U.S. Pat. No. 5,991,488, one way to explain the appearance of an s-polarized resonance component in a conventional SPR experiment as a consequence of adding a dielectric layer 32 onto the metal surface 18 (FIG. 2) is through the application of the electromagnetic field theory to thin-film systems (Macleod, H. A., *Thin Film Optical Filters,* Adam Hilger, Bristol, 1986). For a surface wave to be confined to the metal surface, the admittance exhibited by the adjoining medium must be positive imaginary and of magnitude very close to that of the extinction coefficient k of the metal (i.e., only materials with a small value of the refractive index n and a large value of k will generate a surface wave). For a metallic film, this condition is fulfilled only for p-polarization and a very narrow range of angles of incidence. Coupling of the incident light to the surface wave results in the sharp dip in total internal reflectance that is characteristic of the resonance effect. For s-polarization the admittance is always negative imaginary and, therefore, there is normally no corresponding resonance. However, in the coupled plasmon-waveguide resonance device of the invention the dielectric overcoat layer 32 (or system of layers 32,38) is used to transform the admittance of the emergent medium so that the admittance presented to the metal is positive imaginary for both s- and p-polarization. Depending on the characteristics of the admittance-matching dielectric overcoat (i.e., $n_d$, $k_d$, and $t_d$ values), the system can produce a narrowing or a broadening of the range of angles over which the necessary coincidences are achieved, and hence a similar broadening or narrowing of the resonances. Examination of the distribution of electric field amplitudes through the system shows that the admittance-matching layers are important components of the resonant system, rather like cavity layers in narrowband filters or thin-film waveguides in optical couplers. Thus, the term coupled plasmon-waveguide resonance has been introduced to distinguish this resonance phenomenon from conventional surface plasmon resonance.

Since the added dielectric layer or layers of the CPWR invention make it possible to produce resonance with either s- or p-polarized light, it is desirable to select the dielectric thickness $t_d$ such that both resonance effects fall within the observable range for the system. Thus the same device can be utilized to obtain two sets of measurements from the same sample.

A large variety of dielectric overcoat film combinations (32,38) exists that can be used in particular applications. In essence, any one layer of dielectric or combination of dielectric layers that satisfy the refractive index, extinction coefficient, and thickness requirements for producing resonance at incident angles (for a given wavelength) or at wavelengths (for a given incident angle) within the observable range is suitable for practicing the invention. For example, these materials include $MgF_2$, $Al_2O_3$, $LaF_3$, $Na_3AlF_6$, ZnS, $ZiO_2$, $Y_2O_3$, $HfO_3$, $Ta_2O_5$, ITO, and nitrites or oxy-nitrites of silicon and aluminum, which are all normally used in optical applications.

Measurements using the CPWR devices of the present invention are made in the same way as with conventional SPR techniques. As well understood in the art, the attenuated total reflection method of coupling the light into the deposited thin multilayers is used, thereby exciting resonances that result in absorption of the incident radiation as a function of either the light incident angle α (with a monochromatic light source), or light wavelength λ (at constant incident angle), with a consequent dip in the reflected light intensity.

Figure 3:
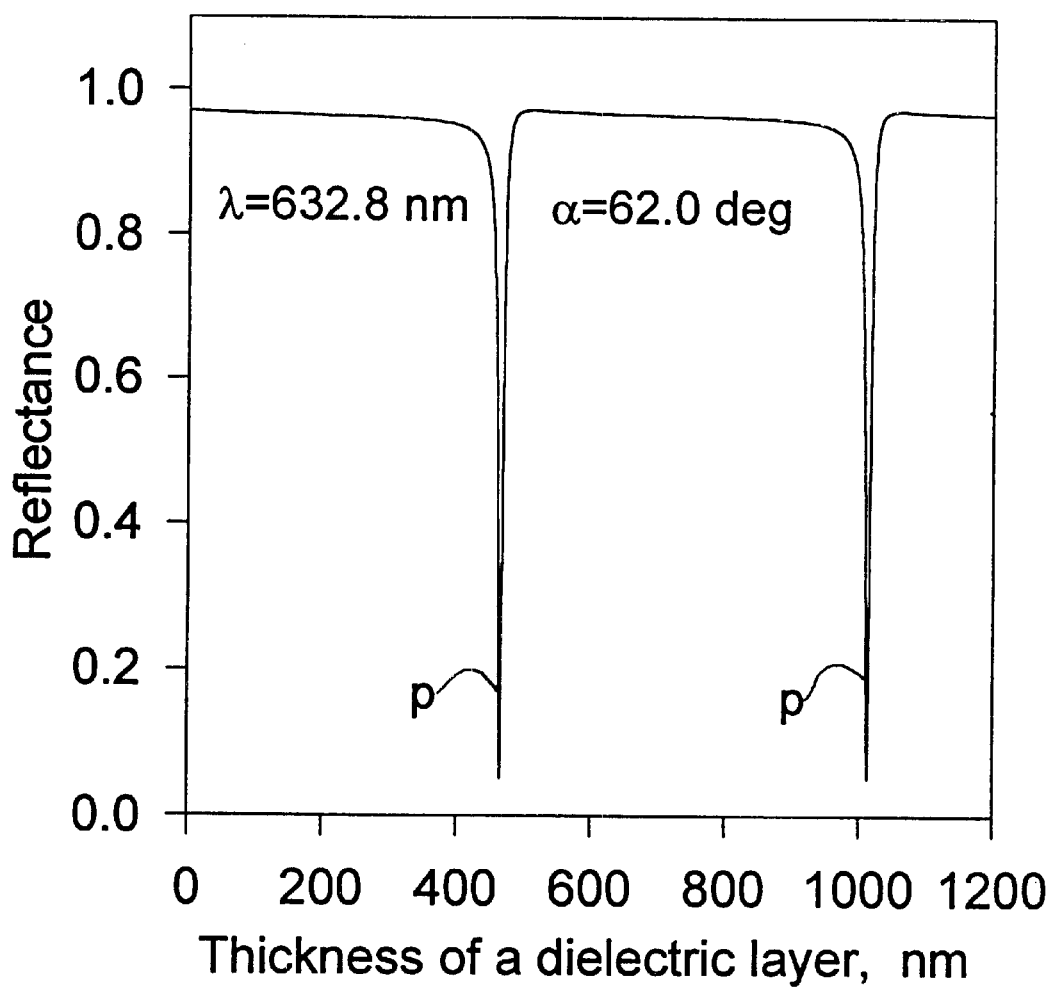
FIG. 3 shows resonance spectra presented as reflected light intensity as a function of the protective $SiO_2$ layer thickness, with p-polarized light and incident angles arbitrarily chosen in the range of usual values for SPR spectroscopy.
Figure 4:
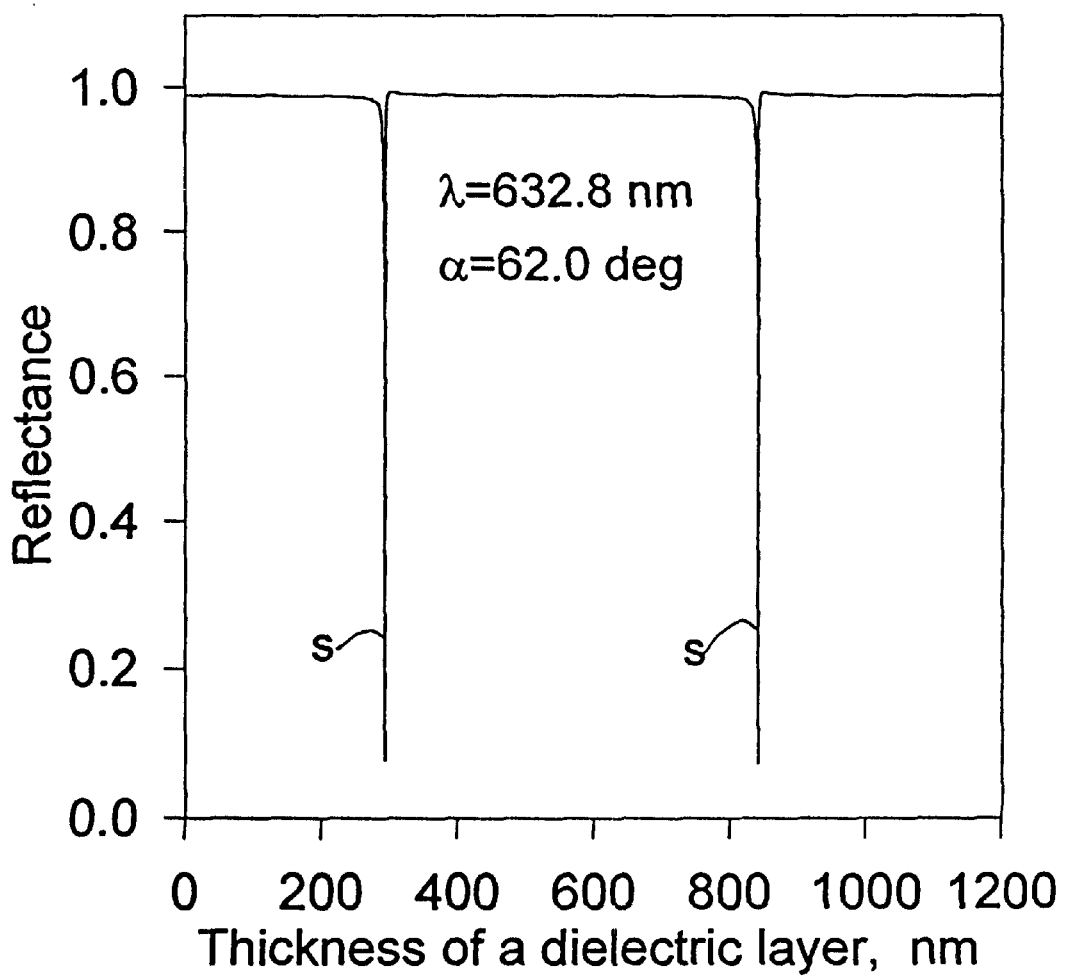
FIG. 4 shows resonance spectra presented as reflected light intensity as a function of the protective $SiO_2$ layer thickness with s-polarized light.

Thus, under appropriate experimental conditions, which are determined by the system's parameters, the devices 30 and 40 of the present invention can be excited by either p- or s-polarized light to resonantly absorb the incident light energy. FIG. 3 illustrates such resonances measured as reflected light intensity as a function of the thickness of the $SiO_2$ dielectric layer 32, obtained with p-polarized light (λ=632.8 nm) in the arrangement shown in FIG. 1 and with an incident angle α (62 degrees) arbitrarily chosen in the typical observable range for a glass-prism/aqueous-emerging-medium system (about 61 to 90 degrees). Similarly, FIG. 4 illustrates resonances measured as a function of the thickness of the $SiO_2$ layer with s-polarized light. The two resonances are separated and occur at different dielectric thicknesses, but these figures demonstrate that it is possible to adjust the thickness of the overcoat layer 32 to obtain both s- and p-resonances with the same device. The apparatus shown in FIG. 1, with a $SiO_2$ layer 32 460 nm thick applied over a 50 nm silver layer 12, and that of FIG. 2, with a combination of a 50 nm $TiO_2$ layer 32 and a 750 nm layer 38 of $Na_3AlF_6$, represent two examples of devices that exhibit the resonances shown in FIGS. 3 and 4.

Figure 5:
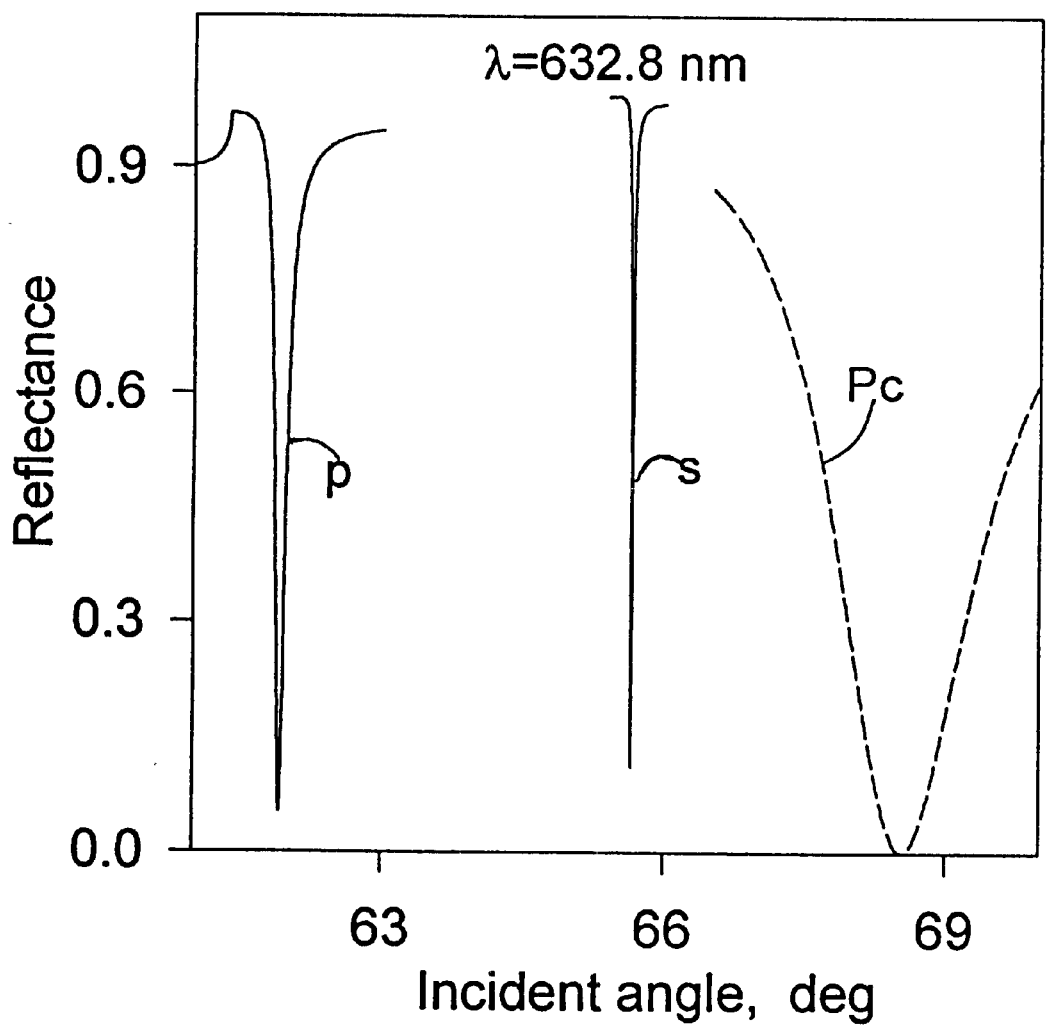
FIG. 5 shows resonance spectra obtained with the device of FIG. 1 presented as reflected light intensity versus incident angles, wherein reference symbols p and s identify curves generated with p- and s-polarized light, respectively, and a dashed curve $P_c$ shows a much broader SPR spectrum obtained with a conventional setup without the dielectric overcoat of the invention.
Figure 6:
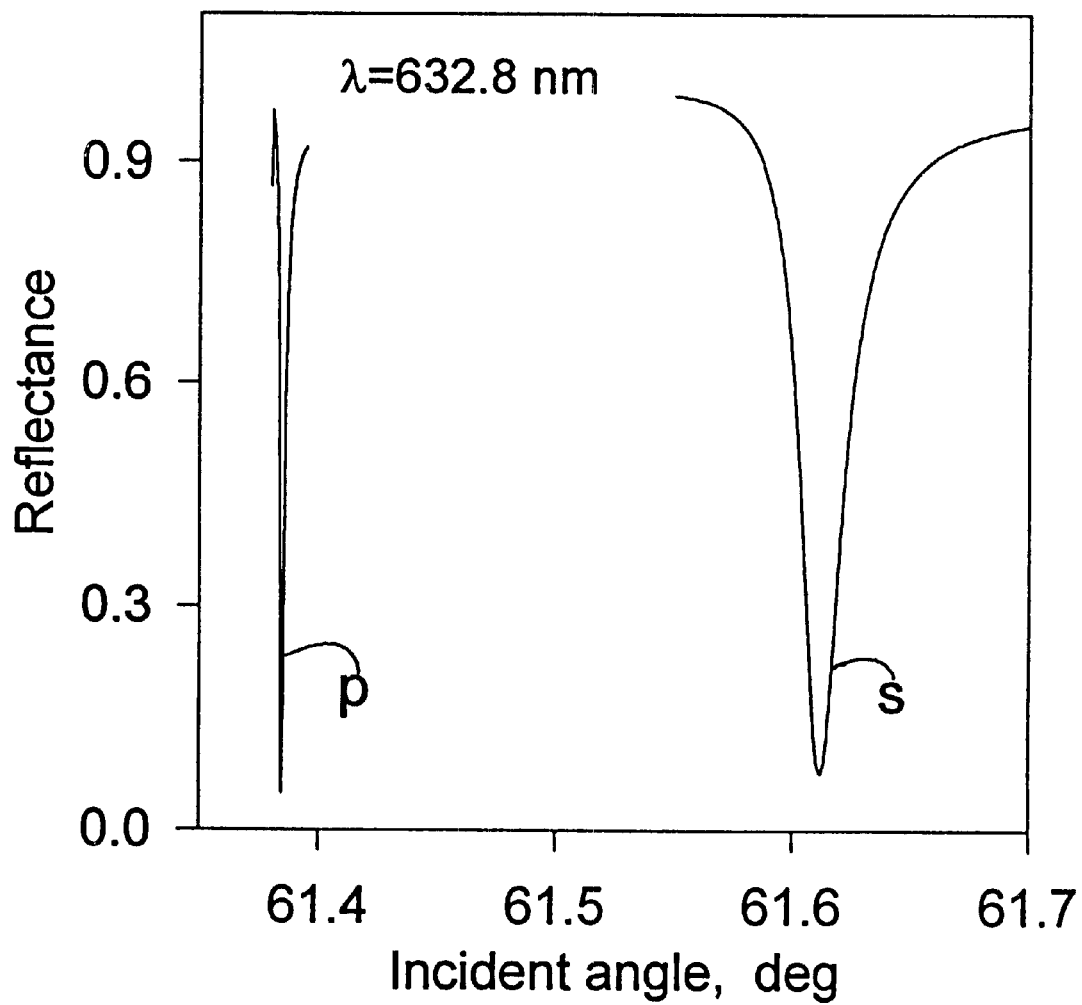
FIG. 6 shows resonance spectra obtained with the device of FIG. 2 presented as reflected light intensity versus incident angles.

FIG. 5 illustrates surface resonances measured as reflected light intensity as a function of the incident angle α with the apparatus 30 of FIG. 1, wherein reference symbols p and s identify curves generated with p- and s-polarized light, respectively. The dashed curve $P_c$ shows the much broader SPR spectrum obtained with the same silver layer of the device in FIG. 1 but with a conventional setup without the dielectric overcoat 32. FIG. 6 illustrates similar results obtained with the apparatus 40 of FIG. 2.

These spectra show that the dielectric layer or layers add two very important features to conventional SPR and LRSPR resonance devices and procedures. The first is the additional spectroscopic dimension provided by generating a second type of resonance with different polarization (the s-polarized component). The second is the increased sensitivity resulting from the greatly decreased half-width of both s- and p-polarized resonances (as clearly seen in FIG. 5). Furthermore, the resonance half-width, and therefore the spectral sensitivity of the apparatus, can be adjusted by judiciously selecting appropriate overcoating layers and polarization mode of operation to meet specific experimental needs, as illustrated by the two sets of results shown in FIGS. 5 and 6. For example, these spectra show that the two dielectric layer designs of FIGS. 1 and 2 produced opposite spectral sensitivity. The device 30 yielded an s-spectrum narrower than the p-spectrum, whereas the opposite was true for the design of the device 40.

Figure 7:
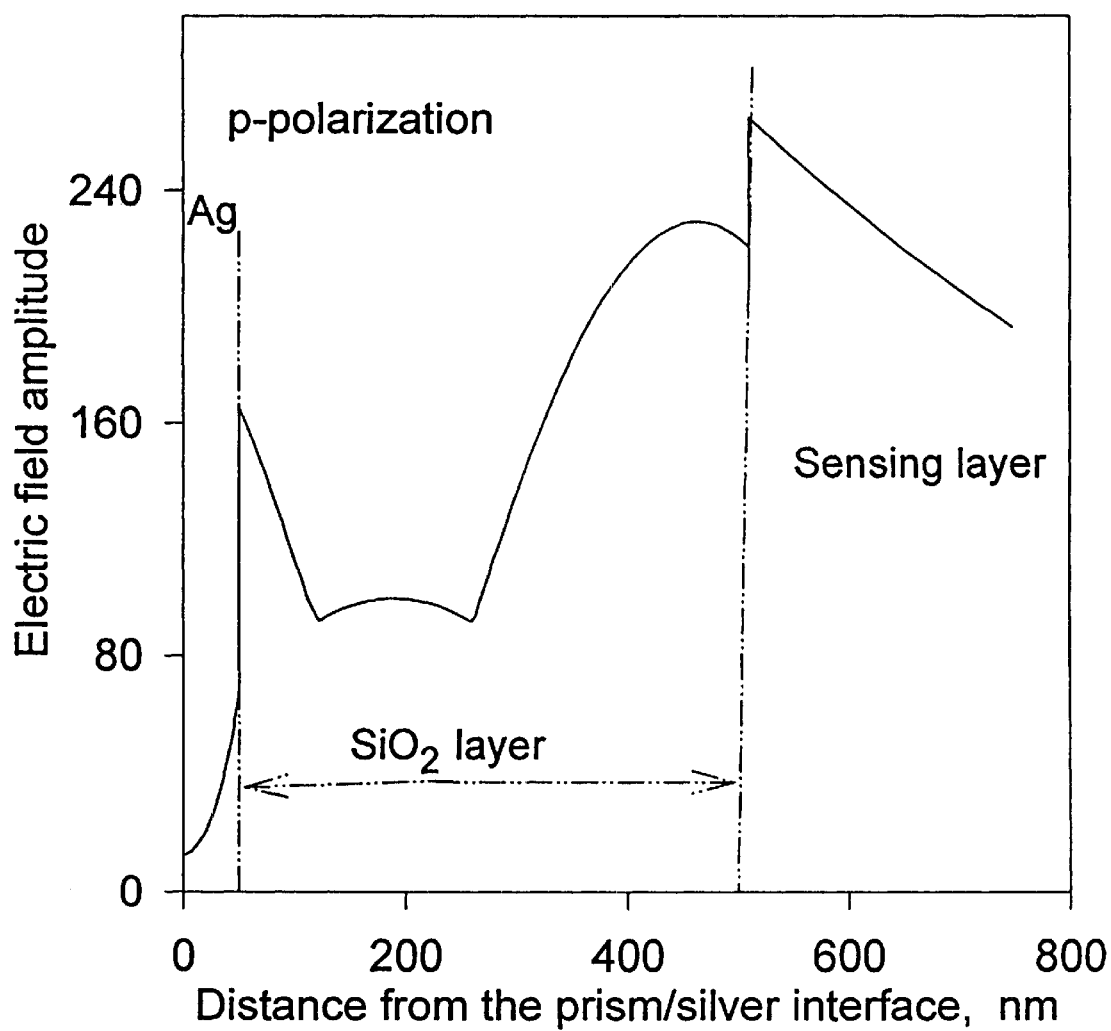
FIG. 7 shows the amplitude of the electric fields within a silver layer, an $SiO_2$ film, and a sensing layer for p-polarized light as a function of the distance from the glass-metal interface for the device shown in FIG. 1.
Figure 8:
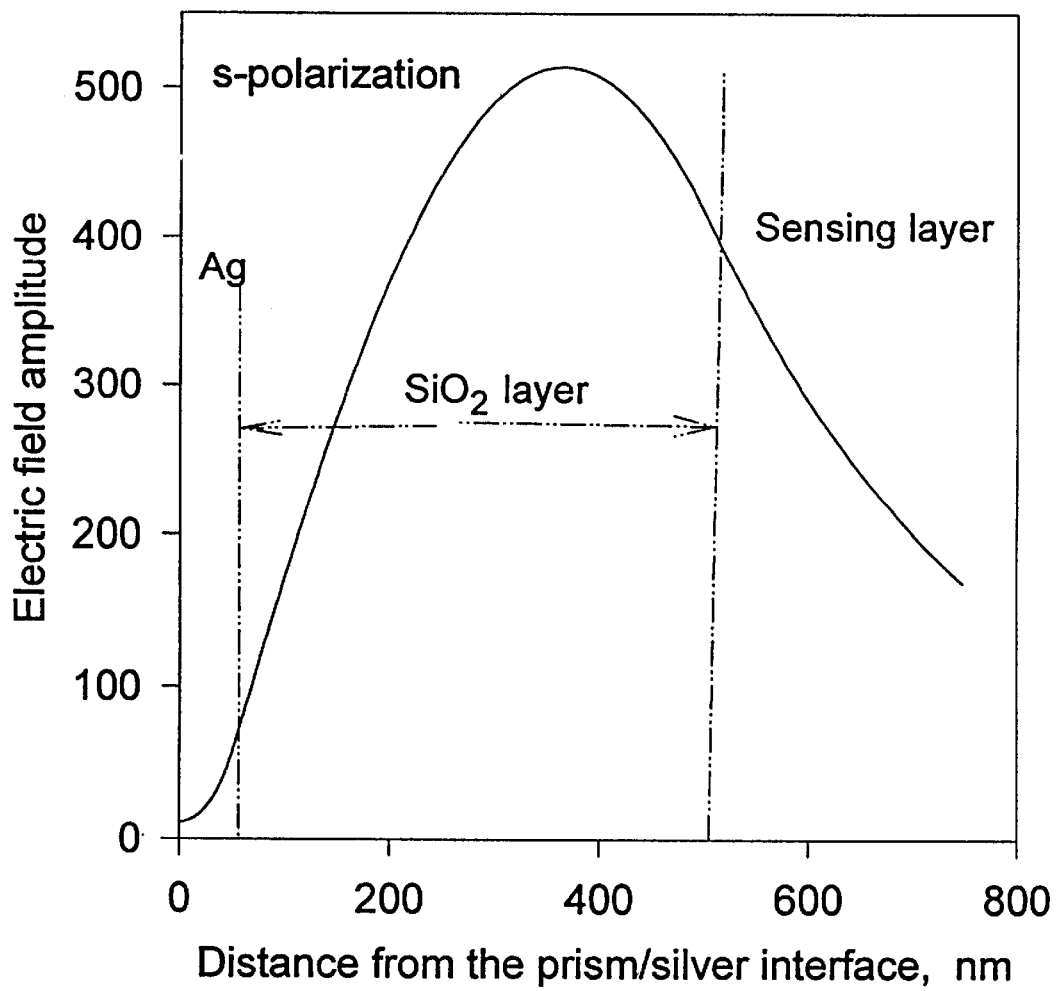
FIG. 8 shows the amplitude of the electric fields within a silver layer, an $SiO_2$ film, and a sensing layer for s-polarized light as a function of the distance from the glass-metal interface for the design shown in FIG. 1.

The overall sensitivity of the devices of the invention includes the sensitivity of the shift of the minimum resonance angle, which is determined in principle by the refractive index and thickness of the sensing layer 34 (for example a lipid bilayer deposited on the surface of the dielectric overcoat 32, as shown in FIG. 1). It also includes the sensitivity to the change in the shape of the resonance spectrum, which depends mainly on the light absorption (and/or scattering) properties of the sensing layer 32. Both of these parameters, i.e., the minimum resonance angle and the shape of the spectrum as defined by its depth and width, are dependent upon the form of the quasi-modes of the electromagnetic field generated in the combination of layers designed according to the invention. FIGS. 7 and 8 show the electric field distributions for p- and s-polarizations, respectively, obtained with the interface of the device 30 of FIG. 1. The figures show that the electric field at the outer interface between the dielectric 32 and the sensing layer 34 is higher by a factor of about 50 for the s-component, and about 25 for the p- component in comparison with that at the entrance interface between the glass 16 and the metal layer 12. As a result of these properties and the corresponding higher sensitivity of the devices of the present invention, the three parameters that determine the resonance spectrum (thickness $t_e$, refractive index $n_e$, and extinction coefficient $k_e$ of the sensing layer 34) can be obtained with accuracies better than 1 Å, 0.001, and 0.002, respectively, for a sensing layer whose thickness is only 5 nm, a value comparable with the thickness of a lipid membrane (see Salamon, Z., Y. Wang, J. L. Soulages, M. F. Brown, and G. Tollin, "Surface Plasmon Resonance Spectroscopy Studies of Membrane Proteins: Transducin Binding and Activation by Rhodopsin Monitored in Thin Membrane Films," *Biophys. J.,* 71: 283–294, 1996; Salamon, Z. and G. Tollin, "Surface Plasmon Resonance Studies of Complex Formation Between Cytochrome c and Bovine Cytochrome c Oxidase Incorporated into a Supported Planar Lipid Bilayer. I: Binding of Cytochrome c to Cardiolipin/Phosphatidylcholine Membranes in the Absence of Oxidase," *Biophvs. J.,* 11:845–857, 1996; and Salamon, Z. and G. Tollin, "Surface Plasmon Resonance Studies of Complex Formation Between Cytochrome c and Bovine Cytochrome c Oxidase Incorporated into a Supported Lipid Bilayer. II: Binding of Cytochrome c to Oxidase-Containing Cardiolipin/phosphatidylcholine Membranes," *Biophys. J.* 71: 858–867, 1996). In practical terms, this means that in many cases the limitation of accuracy in the procedure will result not from the measuring technique itself but from the ability to generate a thin sensing film in a reproducible manner.

Figure 9:
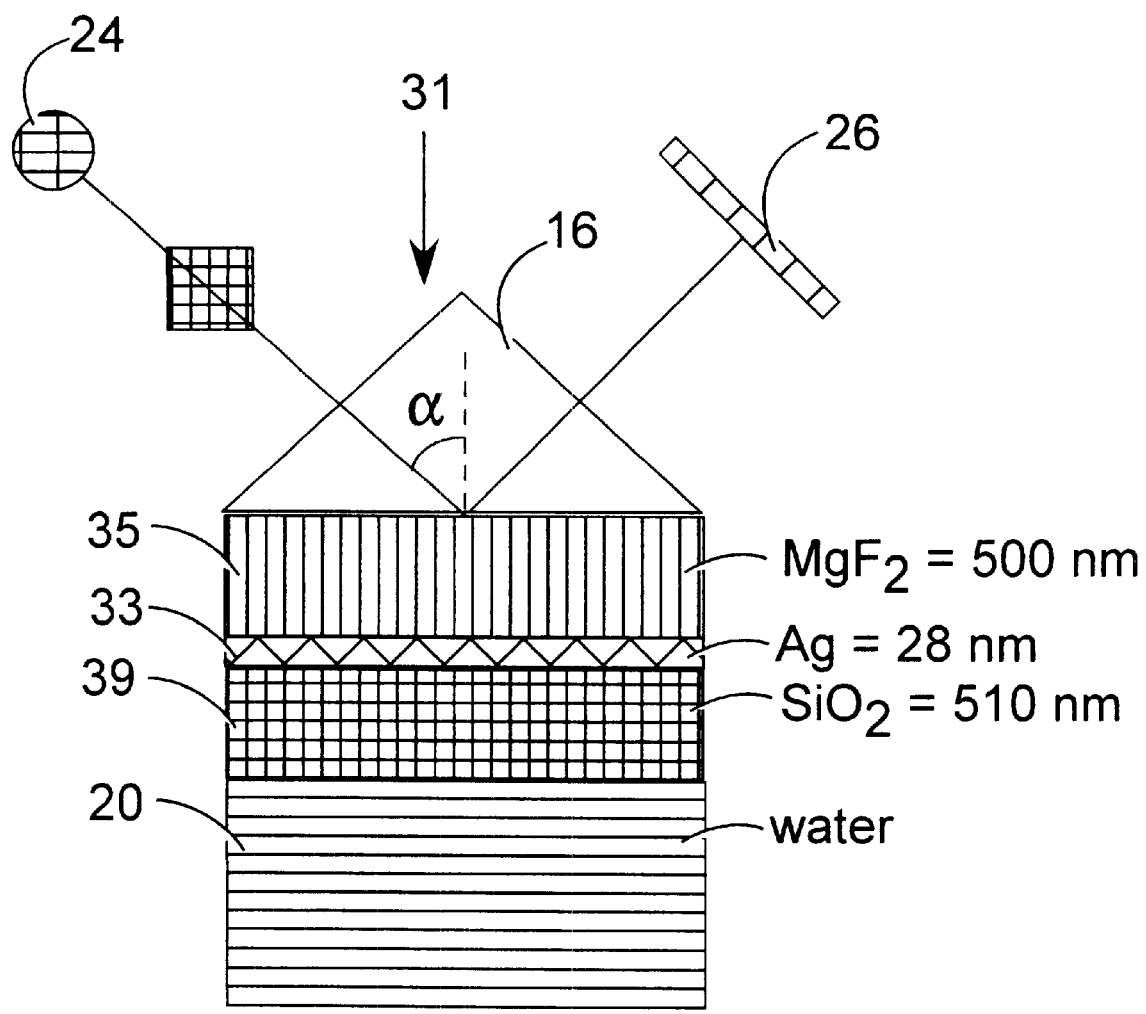
FIG. 9 is a schematic view of an embodiment of a long-range coupled plasmon-waveguide resonance spectroscopic tool according to the invention in an attenuated total reflection measuring system, wherein a 500 nm dielectric layer separates a glass prism from a 28 nm-thick silver layer, and the dielectric of the invention consists of a 510 nm-thick $SiO_2$ film.

FIG. 9 illustrates the invention implemented on a conventional long-range SPR device 31 in a visible-light embodiment. The device 31 contains a metallic (or semiconductor) layer 33 (or layers), typically between 15 and 28 nm thick, formed from either gold or silver deposited on a relatively thick dielectric layer or layers 35 with a refractive index n smaller than that of the glass prism 16 (for example, a 500 nm $MgF_2$ layer, constituting the long-range feature of the device) interposed between the metal layer 33 and the glass prism or grating 16. A 510 nm $SiO_2$ layer 39 on the emergent side of the metal layer 33 provides the dielectric layer of the invention for generating a coupled surface plasmon waveguide.

Figure 10:
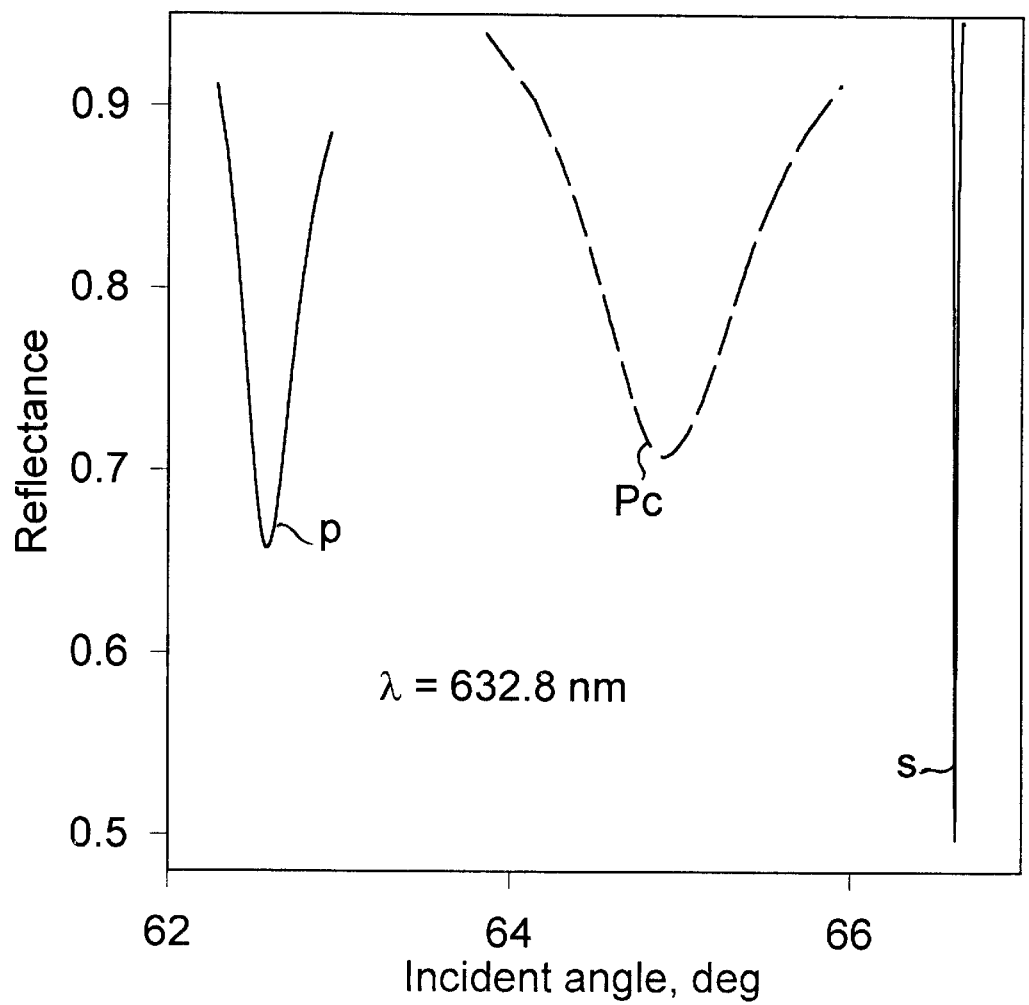
FIG. 10 shows resonance spectra obtained with the device of FIG. 9 presented as reflected light intensity versus incident angles, wherein reference symbols p and s identify curves generated with p- and s-polarized light, respectively, and the dashed curve $p_c$ shows a much broader SPR spectrum obtained with a conventional setup without the dielectric overcoat of the invention.

FIG. 10 illustrates surface resonances measured as reflected light intensity as a function of the incident angle α with the apparatus 31 of FIG. 9, wherein reference symbols p and s identify curves generated with p- and s-polarized light, respectively. The dashed curve $p_c$ shows the much broader LR-SPR spectrum obtained with the same long-range dielectric/silver layer of the device in FIG. 9, but with a conventional setup without the dielectric overcoat 39.

As one skilled in the art would clearly understand, the heart of the invention lies in the discovery that the addition of a dielectric layer interposed between the metallic film and the emergent medium of a surface plasmon resonance device of any type (whether conventional or long-range; or in Kretschmann, Otto or other prism or grating arrangement) introduces a waveguide function that is coupled to plasmon resonances and, therefore, expands conventional SPR (including conventional long-range SPR) into CPWR (or long-range CPWR). In addition, it makes it possible to judiciously select thicknesses and optical parameters of the materials that permit testing with both p- and s-polarized light.

Because of its characteristics, the CPWR aspect of the present invention provides significant advantages over alternative techniques for the detection and measurement of small optical changes based on optical waveguides. The coupling arrangements are simple and convenient. Moreover, the geometric arrangement in CPWR spectroscopy is characterized by a complete isolation of the optical probe from the system under investigation, as is also the case in conventional SPR spectroscopy.

Using the straight CPWR model for an example, the three optical parameters ($n_d$, $k_d$, $t_d$) characterizing a deposited dielectric film 32 (or combination of films 32,38) can be evaluated for both polarizations, at different angles of light incidence, and using different light wavelengths. With these experimental data on hand, it is possible to characterize all of the structural parameters of thin films 34 under investigation, i.e., thickness, mass distribution within the film, orientation of molecules (by measuring the anisotropy in $n_e$), and the orientation of chromophores attached to the molecules within the sensing layer (by measuring the anisotropy of $k_e$). All of these characterizations can be obtained using a single device covered with a sensing layer 34, and using a measurement method that involves only a determination of reflected light intensity under total internal reflection conditions. Details of experimental techniques employed to measure the resonance spectrum are given in Salamon and Tollin (199), supra; Salamon et al. (1996), supra; Salamon et al., "Plasmon Resonance Spectroscopy: Probing Molecular Interactions within Membranes," Trends in Biochemical Sciences, 24, 213–219 (1999); Salamon et al., "Surface Plasmon Resonance, Theory," Encyclopedia of Spectroscopy & Spectrometry, Academic Press, Vol. 3, 2311–2319; and Salamon et al., "Surface Plasmon Resonance: Applications," Encyclopedia of Spectroscopy & Spectrometry, Academic Press, Vol. 3, 2294–2302.

Furthermore, because the electromagnetic field decays exponentially within the emerging medium (see FIGS. 7 and 8), the measurement is sensitive only to the interface region between the dielectric overcoat and the emerging medium, and is not affected by the bulk properties of the medium.

There is no limitation on the dielectric materials that can be used in the coatings 32,38 of the invention, as long as the optical characteristics are favorable, as explained above. Therefore, the dielectric film can be formed from any number of layers 32,38 designed and optimized for different uses. This feature is especially important in various sensor applications, where the dielectric overcoat can also be designed to adsorb and immobilize the sensing material either on its surface or within its interior. It is noted that the effects of the dielectric overcoat of the invention are not diminished by the addition of a very thin (1–5 nm) layer of gold or other metal at the interface with the emerging medium for the purpose of fixating the analyte to the sensing device, as already done with conventional SPR devices. Such a combination of properties in one interface permits the construction of a durable sensor device with very high sensitivity and an expanded dynamic range of measurements.

Although the features of the resonance spectrum produced by CPWR can be employed in a variety of different ways, one of the most fruitful applications lies in biophysical and biochemical studies of the structural properties of proteolipid assemblies. Studies of the microscopic structure of lipid membranes and interacting lipid-protein films represents a technically difficult challenge because they consist of very thin layers comprising only one or two monolayers. In addition, they contain relatively small amounts of material located at the interface between two immiscible phases, and may be labile and structurally heterogeneous. As a result, only a limited number of studies have been made of lipid and/or protein orientation in molecular films.

Our referenced patent reports results that clearly demonstrate that CPWR spectroscopy provides a useful new technique for obtaining information about molecular assemblies which can be immobilized at a dielectric/water interface. Three major improvements over conventional SPR methodologies have been documented: increased spectral resolution, improved sensitivity, and the ability to measure anisotropy in both n and k. Furthermore, CPWR is applicable to a wide range of materials, including, without limitation, lipid membranes that have either integral membrane proteins incorporated into them or peripheral membrane proteins bound to their surface.

The improvement of this disclosure lies in the idea of extending the range of application of surface-plasmon-resonance sensing by enabling testing outside the range of visible light. This objective is particularly desirable for biochemical and biological applications to measure phenomena induced by monochromatic light in such spectral ranges. Since the index of refraction and the extinction coefficient of a material are functions of wavelength, it follows that SPR techniques can be practiced also in the UV and IF spectral ranges if a metal or semiconductor material with sufficiently low n and sufficiently high k is found. Accordingly, we searched and tested numerous metals and identified aluminum and copper as suitable for implementing SPR devices in the UV and IF ranges, respectively.

Figure 11:
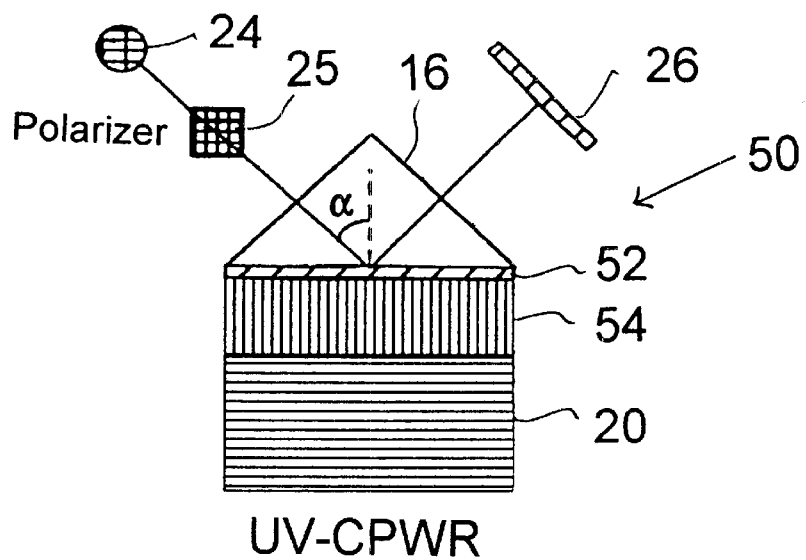
FIG. 11 is a schematic view of an embodiment of an ultraviolet coupled plasmon-waveguide resonance spectroscopic tool according to the invention in an attenuated total reflection measuring system, wherein an $SiO_2$ prism is coated with a 20 nm-thick aluminum layer protected by a 210 nm-thick $SiO_2$ film.
Figure 12:
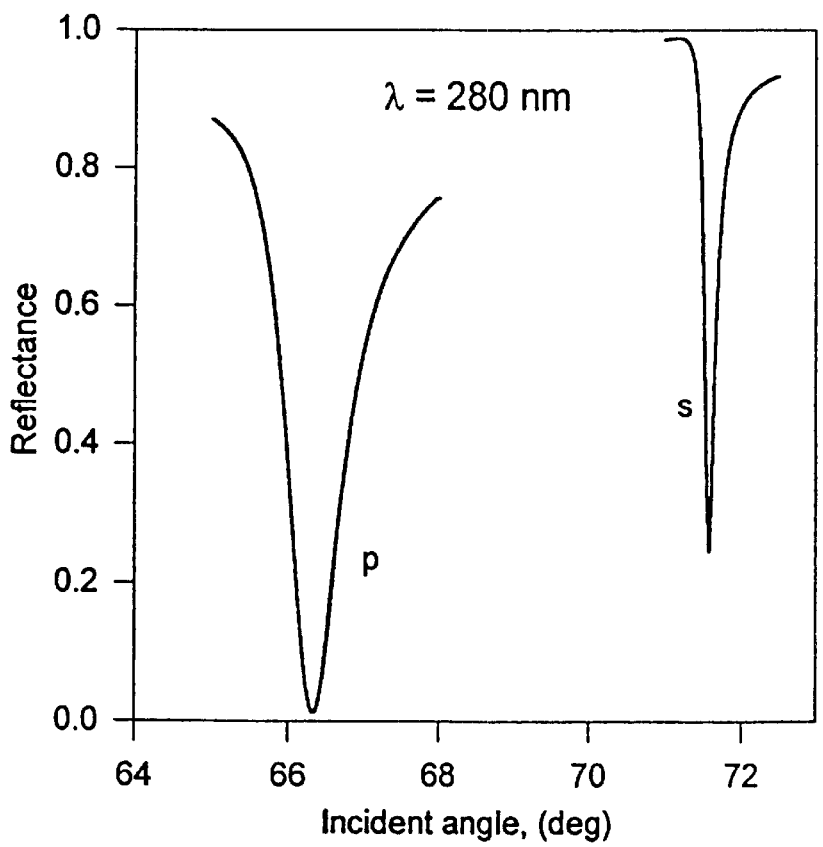
FIG. 12 shows resonance spectra obtained with the device of FIG. 11 presented as reflected light intensity versus incident angles.

FIG. 11 illustrates an ultraviolet CPWR device 50 where the silver/gold layer of FIG. 1 is replaced with a 20 nm-thick aluminum film 52 covered with a 210 nm-thick silica layer 54. The entrant medium 16 is also $SiO_2$. FIG. 12 shows the resonance spectra obtained with this device using ultraviolet light ($\lambda$=280 nm) and both p- and s-polarizations.

Figure 13:
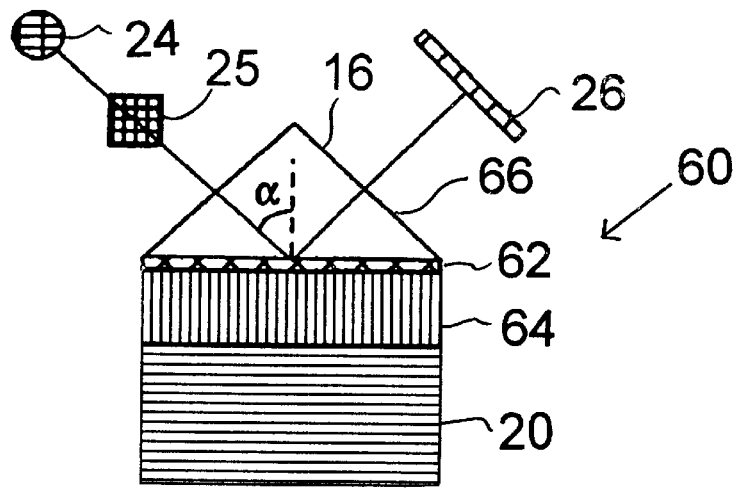
FIG. 13 is a schematic view of an embodiment of an infrared coupled plasmon-waveguide resonance spectroscopic tool according to the invention in an attenuated total reflection measuring system, wherein an $SiO_2$ prism is coated with a 20 nm-thick copper layer protected by a 1280 nm-thick $SiO_2$ film.
Figure 14:
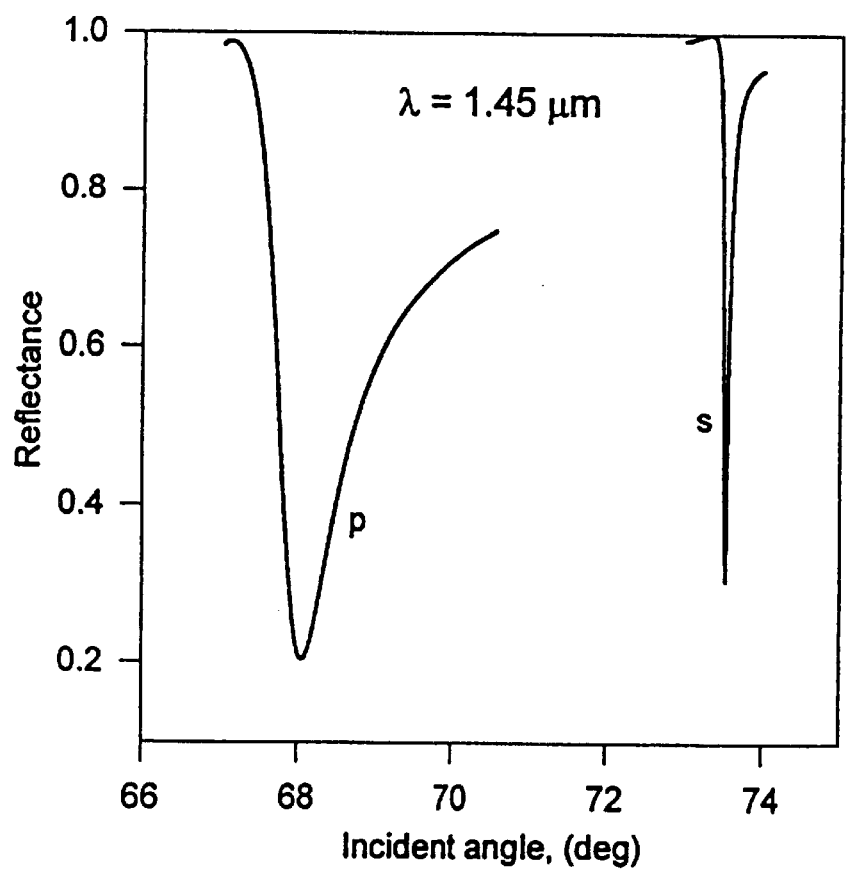
FIG. 14 shows resonance spectra obtained with the device of FIG. 13 presented as reflected light intensity versus incident angles.

FIG. 13 illustrates an infrared CPWR device 60 using a 20 nm-thick copper 62 film coated with a 1280 nm $SiO_2$ layer 64. The entrant medium 66 is also $SiO_2$. Because of the n and k properties of copper, the device can be used in a wide region of the IR spectrum. FIG. 14 shows the resonance spectra obtained with this device using infrared light ($\lambda$=1.45 $\mu$m) and both p- and s-polarizations.

The devices of FIGS. 11 and 13 are based on CPWR embodiments of conventional SPR devices, but it is clear that both of these spectral ranges (UV and IR) can also be covered utilizing long-range surface plasmon resonance by adding a coupling dielectric layer to the metal layer as disclosed herein.

Figure 15:
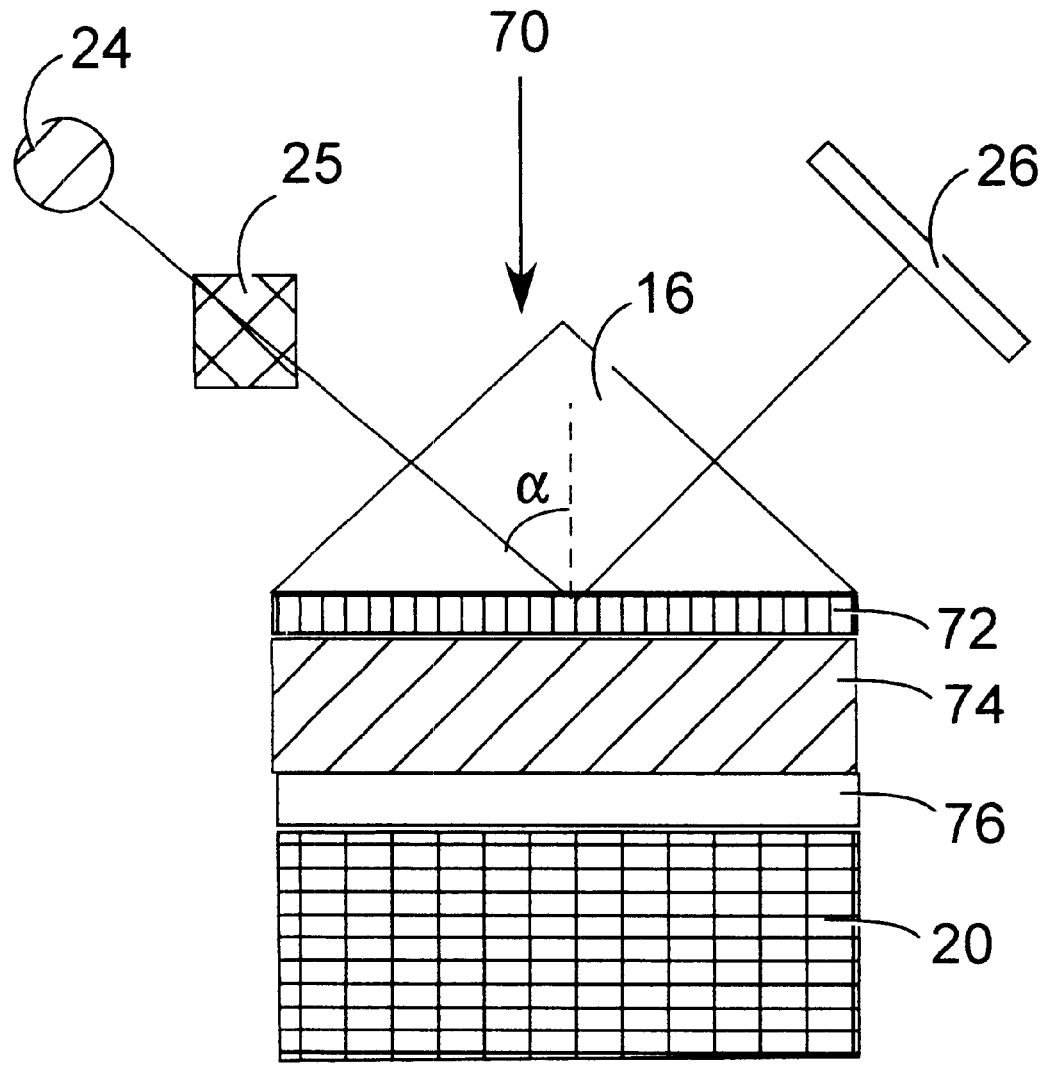
FIG. 15 is a schematic view of another embodiment of a coupled plasmon-waveguide resonance spectroscopic tool according to the invention, wherein a glass prism coated with a 50 nm-thick silver layer contains two dielectric layers; one layer of 410 nm $SiO_2$ protects the silver film and is coated with a second 20 nm layer of semiconductive ITO.
Figure 16:
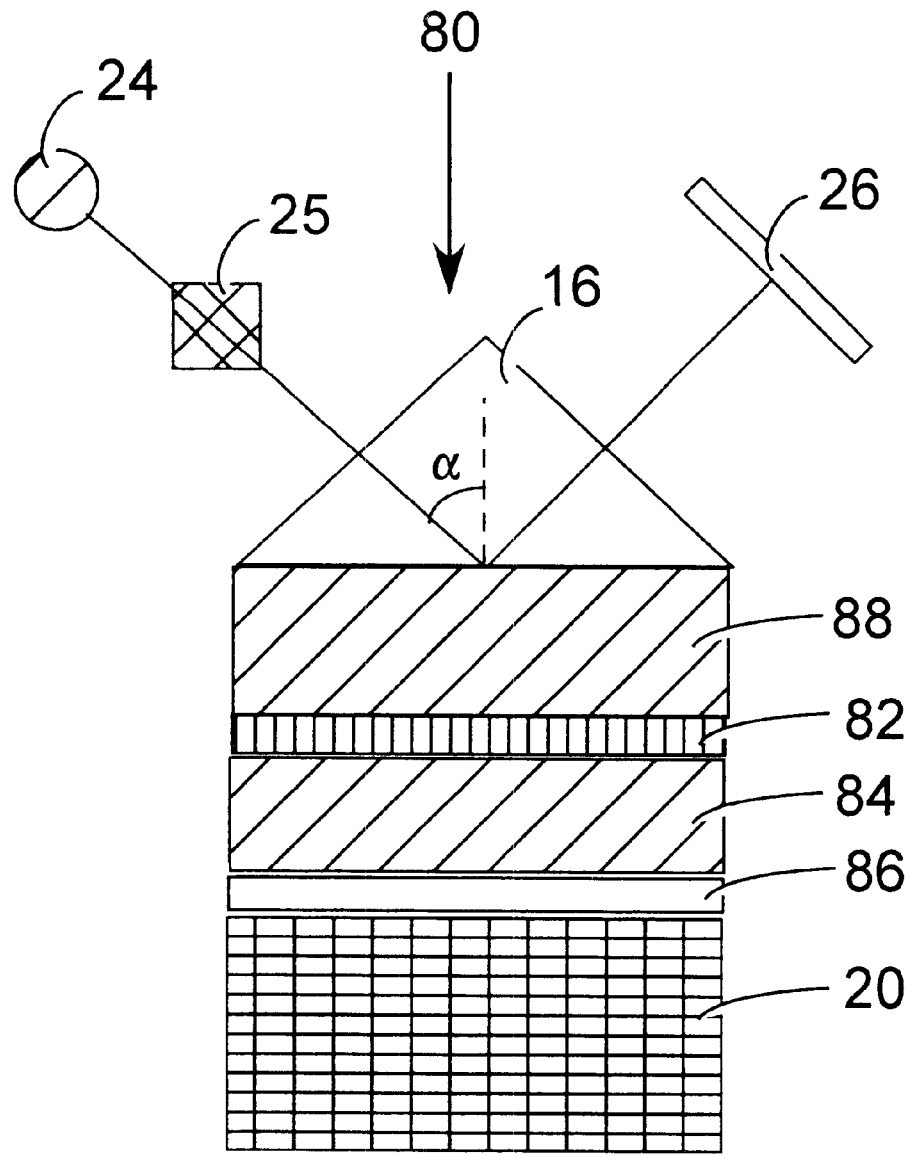
FIG. 16 is a schematic view of a long-range coupled plasmon-waveguide resonance spectroscopic tool according to the invention, wherein a glass prism is coated with a 500 nm-thick dielectric inner layer of $MgF_2$, a 28 nm-thick silver layer, a first outer layer of 450 nm $SiO_2$, and a second 20 nm outer layer of semiconductive ITO.
Figure 17:
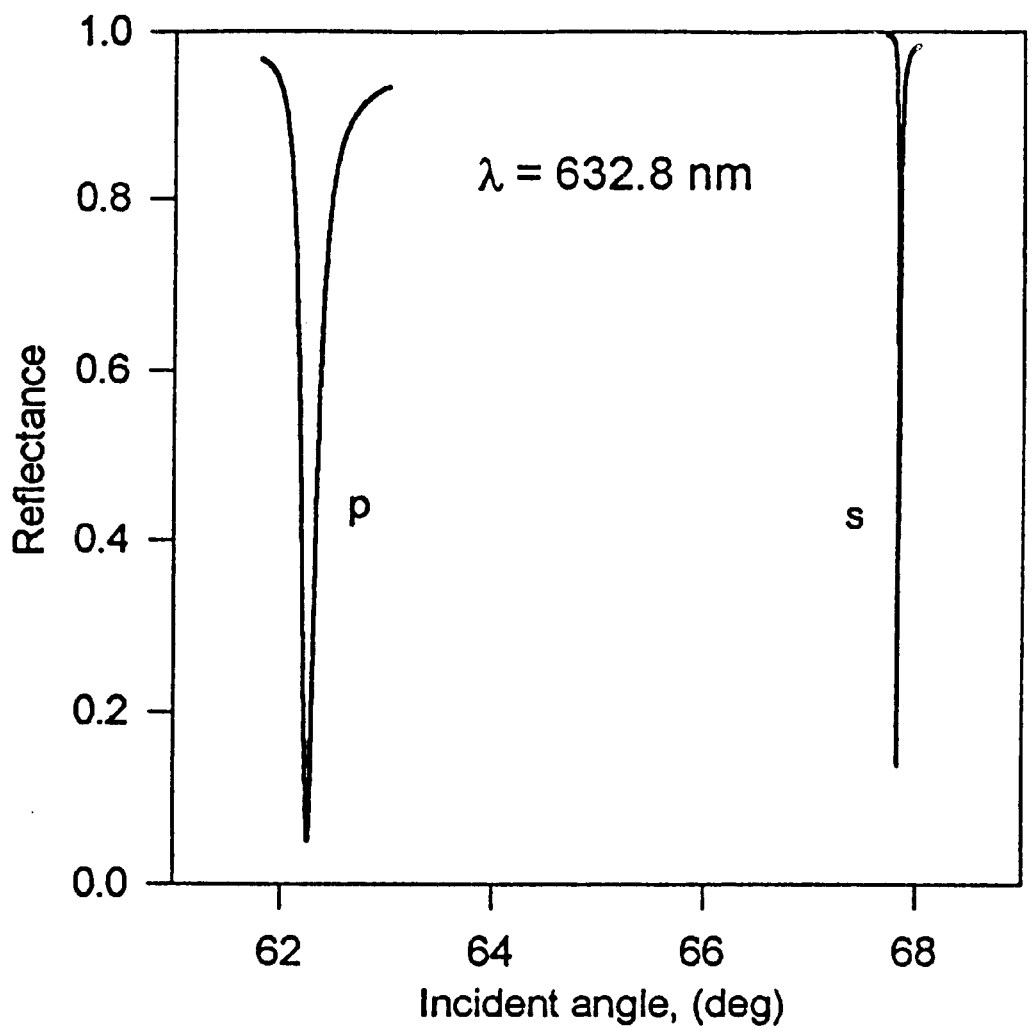
FIG. 17 shows resonance spectra obtained with the device of FIG. 15 presented as reflected light intensity versus incident angles.
Figure 18:
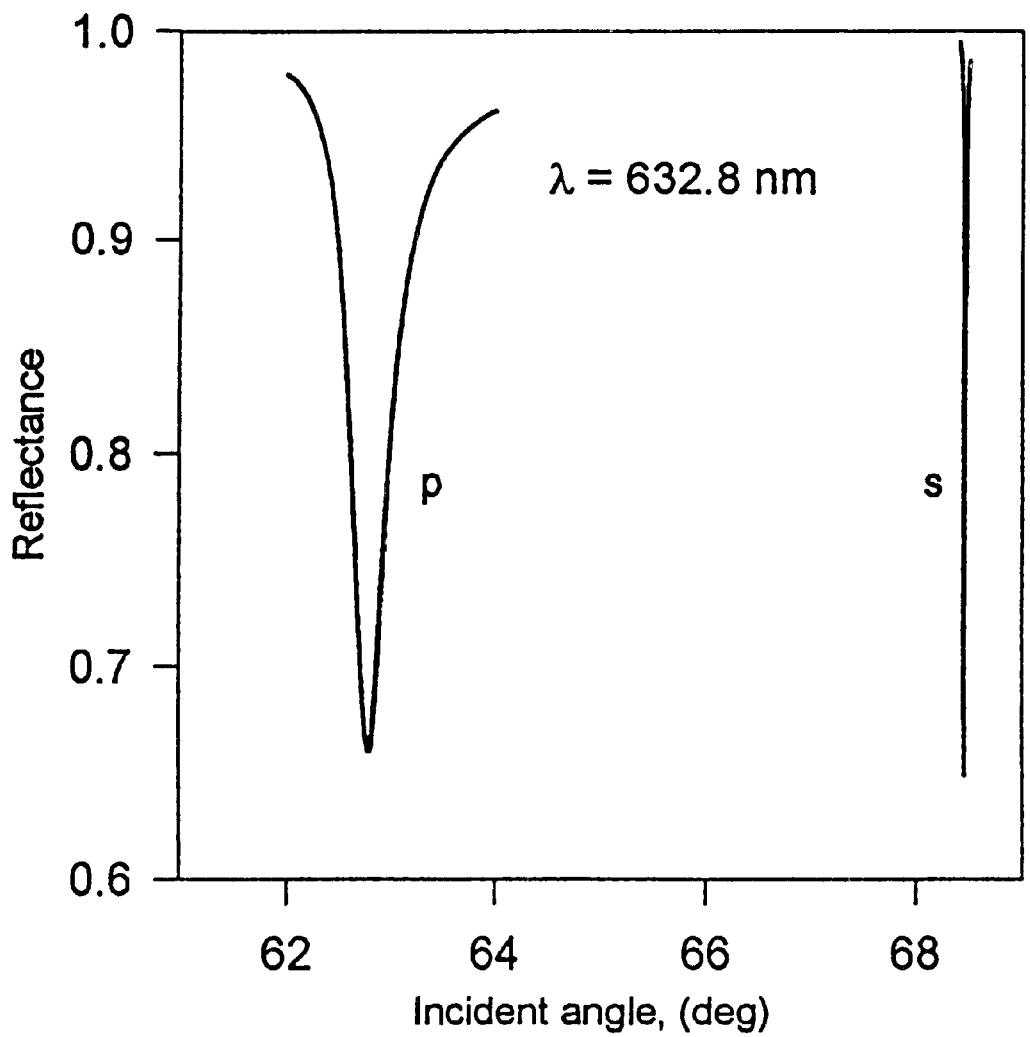
FIG. 18 shows resonance spectra obtained with the device of FIG. 16 presented as reflected light intensity versus incident angles.

FIGS. 15 and 16 show typical examples of coupled plasmon-waveguide resonance devices based on coupling, respectively, conventional surface plasmon resonance or long-range surface plasmon resonance with an additional semiconductor layer providing an electrode for electrical measurements. In both examples the emergent medium is water and the entrant medium is a glass prism. FIGS. 17 and 18 show the resonance curves obtained with the devices of FIGS. 15 and 16, respectively, for both p- and s-polarized excitation light.

Both devices consist of surface plasmon and waveguide generating thin-film designs that are combined to allow coupling between these two optical phenomena. The important difference between these two devices lies in the phenomenon by which creation of surface plasmons occurs. In the CPWR device, the surface plasmons are generated by conventional surface plasmon resonance, whereas in the long-range CPWR device they are generated using long-range surface plasmon resonance. This difference is reflected in the design of the thin film assembly presented in FIGS. 15 and 16, as described below.

The CPWR device 70 of FIG. 15 comprises a 50 nm-thick silver film 72 deposited either directly on an entrant medium 16 or on a very thin (on the order of only a few nanometers) layer of additional material (not shown) which is sometimes used to enhance adhering of silver to the entrant medium. This silver film is covered with a dielectric layer that is formed in this example from two layers: a 410 nm-thick silica ($SiO_2$) layer and 20 nm-thick indium tin oxide (ITO) layer 76. This design of the waveguide film is used to demonstrate that the optical CPWR device can also be utilized in electrical measurements by employing an outer semiconducting ITO layer as an electrode.

The long-range CPWR device 80 of FIG. 15 consists of a much thinner silver film 82 (28 nm) than in the CPWR device, which must be placed on a thick dielectric layer 88 with proper optical parameters and thickness to allow excitation of a surface-bound electromagnetic wave on both surfaces of the metal film (e.g., 500 nm-thick $MgF_2$ layer). This is in contrast to the design presented in FIG. 15 where the surface-bound electromagnetic wave is generated only on the outer surface of the silver layer. The metal film is overcoated with a similar thin film waveguide system as presented in FIG. 15, i.e., a 450 nm-thick $SiO_2$ layer 84 coated with a 20 nm-thick ITO film 86.

Thus, it has been shown that by choosing materials with appropriate optical parameters and physical properties it is possible to create a CPWR thin-film assembly to be used in a wide variety of applications. CPWR devices can be designed for use in a wide spectral range, including the visible, ultraviolet and infrared electromagnetic regions. Such devices permit simultaneous measurement of several properties of one molecular species in the presence of multiple molecular species in a thin-film sample. In addition, the dielectric overcoat layer can also be designed to serve both as a waveguide and at the same time as an electrode. This allows the combination of an optical device with an electrical device, capable of monitoring simultaneously electrical characteristics and optical parameters of thin films and interfaces.

Thus, this disclosure expands the application of plasmon resonance techniques beyond the visible electromagnetic spectral range. Furthermore, it enables the use of CPWR devices in both optical and electrical measurements at multiple wavelengths, which allows characterization of the properties of a thin film consisting of a mixture of different molecules by independently measuring the properties of each type of molecule.

Various changes in the details, steps and components that have been described may be made by those skilled in the art within the principles and scope of the invention herein illustrated and defined in the appended claims. For example, other dielectric materials with n and k parameters suitable for the invention could be used. For a given material and other system parameters, a range of thicknesses could be used with equivalent results. For example, the system of FIG. 1 can be implemented with any $SiO_2$ layer greater than 420 nm; the same system can be implemented with any $TiO_2$ layer greater than 750 nm. Similarly, the observable range can be increased or decreased by changing the properties of the prism and/or the emerging medium. For example, changing the prism to a material with n=2.2 would essentially double the observable range from about 61–90 degrees to 35–90 degrees in a system with an aqueous emerging medium.

Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and devices.

We claim:

1. A surface-plasmon-resonance spectroscopic device comprising:
    a light beam directed toward an incident medium;
    a metallic or semiconductor film adjacent to the incident medium;
    a light detector adapted to receive radiation reflected from said film through the incident medium;
    a dielectric member adjacent to the film; and
    an emergent medium with a sample material at an interface of the emergent medium with the dielectric member;
    wherein the dielectric member is selected such that coupled plasmon-waveguide resonance effects are produced within an observable range.

2. The device of claim 1, wherein said film consists substantially of silver or gold and said light beam has a wavelength within the visible range.

3. The device of claim 1, wherein said film consists substantially of aluminum and said light beam has a wavelength within the ultraviolet range.

4. The device of claim 1, wherein said film consists substantially of copper and said light beam has a wavelength within the infrared range.

5. The device of claim 1, wherein said dielectric member is selected from the group consisting of $SiO_2$, $TiO_2$, $MgF_2$, $Al_2O_3$, $LaF_3$, $Na_3AlF_6$, ZnS, $ZiO_2$, $Y_2O_3$, $HfO_3$, $Ta_2O_5$, ITO, and nitrites or oxy-nitrites of silicon and aluminum, and mixtures thereof.

6. The device of claim 1, wherein said dielectric member comprises a first layer of dielectric material having a predetermined density and a second layer of dielectric material having a lower density; the first layer being in contact with said film and the second layer being in contact with said sample material.

7. The device of claim 6, wherein said first layer of dielectric material is selected from said group consisting of $SiO_2$, $TiO_2$, $MgF_2$, $Al_2O_3$, $LaF_3$, $Na_3AlF_6$, ZnS, $ZiO_2$, $Y_2O_3$, $HfO_3$, $Ta_2O_5$, ITO, and nitrites or oxy-nitrites of silicon and aluminum, and mixtures thereof.

8. The device of claim 6, wherein said second layer is a hydrogel material.

9. The device of claim 1, further comprising a layer of semiconductive material between said dielectric member and said emergent medium.

10. The device of claim 1, wherein said sample material comprises a lipid layer.

11. The device of claim 1, wherein said incident medium is either a prism or a grating.

12. A surface-plasmon-resonance spectroscopic device comprising:
    a light beam directed toward an incident medium;
    a metallic or semiconductor film adjacent to the incident medium;
    a light detector adapted to receive radiation reflected from said film through the incident medium;
    a dielectric member adjacent to the film; and
    an emergent medium with a sample material at an interface of the emergent medium with the dielectric member;
    wherein said metallic or semiconductor film is selected in a thickness sufficient to prevent excitation of surface-bound waves on both sides thereof, said dielectric member is selected such that coupled plasmon-waveguide resonance effects are produced within an observable range, said film consists substantially of aluminum, and said light beam has a wavelength within the ultraviolet range.

13. The device of claim 12, further comprising a layer of semiconductive material between said dielectric member and said emergent medium.

14. A surface-plasmon-resonance spectroscopic device comprising:
    a light beam directed toward an incident medium;
    a metallic or semiconductor film adjacent to the incident medium;
    a light detector adapted to receive radiation reflected from said film through the incident medium;
    a dielectric member adjacent to the film; and
    an emergent medium with a sample material at an interface of the emergent medium with the dielectric member;
    wherein said metallic or semiconductor film is selected in a thickness sufficient to prevent excitation of surface-bound waves on both sides thereof, said dielectric member is selected such that coupled plasmon-waveguide resonance effects are produced within an observable range, said film consists substantially of copper, and said light beam has a wavelength within the infrared range.

15. The device of claim 14, further comprising a layer of semiconductive material between said dielectric member and said emergent medium.

16. A long-range surface-plasmon-resonance spectroscopic device comprising:
    a light beam directed toward an incident medium;
    a dielectric layer adjacent to the incident medium:
    a metallic or semiconductor film adjacent to the dielectric layer;
    a light detector adapted to receive radiation reflected from said film through the incident medium;
    a dielectric member adjacent to the film on a side opposite to the dielectric layer; and
    an emergent medium with a sample material at an interface of the emergent medium with the dielectric member;
    wherein said metallic or semiconductor film is selected in a thickness insufficient to prevent excitation of surface-bound waves on both sides thereof, and said dielectric member is selected such that coupled plasmon-waveguide resonance effects are produced within an observable range.

17. The device of claim 16, wherein said film consists substantially of aluminum and said light beam has a wavelength within the ultraviolet range.

18. The device of claim 16, wherein said film consists substantially of copper and said light beam has a wavelength within the infrared range.

19. The device of claim 16, further comprising a layer of semiconductive material between said dielectric member and said emergent medium.

20. A method for measuring a property of a sample material present at an interface of an emerging medium in a surface-plasmon-resonance spectroscopic device, wherein a surface plasmon is excited by a light beam and propagated along a metallic or semiconductor film, comprising the following steps:

(a) coating said film with a dielectric member selected such that coupled plasmon-waveguide resonance effects are produced within an observable range;

(b) placing said dielectric member at said interface of the emerging medium of the surface-plasmon-resonance spectroscopic device; and (c) performing surface-plasmon-resonance spectroscopic measurements according to conventional procedures.

21. A method for measuring a property of a sample material present at an interface of an emerging medium in a surface-plasmon-resonance spectroscopic device, wherein a surface plasmon is excited by a light beam and propagated along a metallic or semiconductor film, comprising the following steps:

(a) coating said film with a dielectric member selected such that coupled plasmon-waveguide resonance effects are produced within an observable range;

(b) placing said dielectric member at said interface of the emerging medium of the surface-plasmon-resonance spectroscopic device; and (c) measuring a radiation reflected through said incident medium to detect an intensity variation as a function of a change in said property of the sample material.

22. The method of claim 21, wherein said sample material comprises a lipid layer adsorbed and immobilizing into said matrix of the second layer of dielectric material.

23. The method of claim 21, wherein said light beam is either s- or p-polarized.

24. The method of claim 21, wherein said dielectric member comprises a first layer of dielectric material having a predetermined density and a second layer of dielectric material comprising a lower-density matrix; the first layer being in contact with said film and the second layer being in contact with said sample material.

25. The method of claim 21, further comprising the steps of placing a layer of semiconductive material between said dielectric member and said emergent medium and of also performing electrical measurements while carrying out step (c).

26. A method for measuring a property of a sample material present at an interface of an emerging medium in a surface-plasmon-resonance spectroscopic device, wherein a surface plasmon is excited by a light beam and propagated along a metallic or semiconductor film sufficiently thick to prevent excitation of surface-bound waves on both sides thereof, comprising the following steps:

(a) coating said film with a dielectric member selected such that coupled plasmon-waveguide resonance effects are produced within an observable range;

(b) placing said dielectric member at said interface of the emerging medium of the surface-plasmon-resonance spectroscopic device;

(c) placing a layer of semiconductive material between said dielectric member and said emergent medium;

(d) performing surface-plasmon-resonance spectroscopic measurements according to conventional procedures; and (e) also performing electrical measurements while carrying out step (d).

27. A method for measuring a property of a sample material present at an interface of an emerging medium in a long-range surface-plasmon-resonance spectroscopic device, wherein a surface plasmon is excited by a light beam and propagated along a metallic or semiconductor film insufficiently thick to prevent excitation of surface-bound waves on both sides thereof, comprising the following steps:

(a) coating said film with a dielectric member selected such that coupled plasmon-waveguide resonance effects are produced within an observable range;

(b) placing said dielectric member at said interface of the emerging medium of the surface-plasmon-resonance spectroscopic device; and (c) performing surface-plasmon-resonance spectroscopic measurements according to conventional procedures.

28. A method for measuring a property of a sample material present at an interface of an emerging medium in a surface-plasmon-resonance spectroscopic device, wherein a surface plasmon is excited by a light beam and propagated along a metallic or semiconductor film sufficiently thick to prevent excitation of surface-bound waves on both sides thereof, comprising the following steps:

(a) coating said film with a dielectric member selected such that coupled plasmon-waveguide resonance effects are produced within an observable range;

(b) placing said dielectric member at said interface of the emerging medium of the surface-plasmon-resonance spectroscopic device; and (c) measuring a radiation reflected through said incident medium to detect an intensity variation as a function of a change in said property of the sample material.

29. A method for measuring a property of a sample material present at an interface of an emerging medium in a long-range surface-plasmon-resonance spectroscopic device, wherein a surface plasmon is excited by a light beam and propagated along a metallic or semiconductor film insufficiently thick to prevent excitation of surface-bound waves on both sides thereof, comprising the following steps:

(a) coating said film with a dielectric member selected such that coupled plasmon-waveguide resonance effects are produced within an observable range;

(b) placing said dielectric member at said interface of the emerging medium of the surface-plasmon-resonance spectroscopic device; and (c) measuring a radiation reflected through said incident medium to detect an intensity variation as a function of a change in said property of the sample material.

30. The method of claim 29, further comprising the steps of placing a layer of semiconductive material between said dielectric member and said emergent medium and of also performing electrical measurements while carrying out step (c).

* * * * *

UNITED STATES PATENT AND TRADEMARK OFFICE
CERTIFICATE OF CORRECTION

PATENT NO.   : 6,421,128 B1
DATED        : July 16, 2002
INVENTOR(S)  : Zdzislaw Salamon et al.

It is certified that error appears in the above-identified patent and that said Letters Patent is hereby corrected as shown below:

<u>Title page,</u>
Add the following Related U.S. Application Data,

-- [60] Continuation-in-part application of 09/448,394, filed on Nov. 23, 1999, now Pat. No. 6,330,387, which is a continuation-in-part of 08/965,733, filed on Nov. 7, 1997, now Pat. No. 5,991,488, and provisional application No. 60/030,768, filed on November 8, 1996. --

Signed and Sealed this

Twelfth Day of November, 2002

*Attest:*

JAMES E. ROGAN
*Attesting Officer*    *Director of the United States Patent and Trademark Office*